US008685099B2

(12) United States Patent
Bhattacharya et al.

(10) Patent No.: US 8,685,099 B2
(45) Date of Patent: Apr. 1, 2014

(54) MULTIPLE COMPONENT OSTEOIMPLANT

(75) Inventors: Jinia Bhattacharya, New York, NY (US); Todd M. Boyce, Matawan, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 935 days.

(21) Appl. No.: 12/190,416

(22) Filed: Aug. 12, 2008

(65) Prior Publication Data

US 2009/0099661 A1 Apr. 16, 2009

Related U.S. Application Data

(60) Provisional application No. 60/955,837, filed on Aug. 14, 2007, provisional application No. 60/980,291, filed on Oct. 16, 2007.

(51) Int. Cl.
*A61F 2/44* (2006.01)
(52) U.S. Cl.
USPC ..................... 623/17.16; 623/17.11
(58) Field of Classification Search
USPC ........................... 623/17.11–17.16
See application file for complete search history.

(56) References Cited

U.S. PATENT DOCUMENTS

| 4,877,020 | A | 10/1989 | Vich |
| 4,950,296 | A | 8/1990 | McIntyre |
| 5,769,897 | A * | 6/1998 | Harle ............................ 424/423 |
| 5,814,084 | A | 9/1998 | Grivas et al. |
| 5,888,228 | A | 3/1999 | Knothe et al. |
| 5,972,368 | A | 10/1999 | McKay |
| 6,159,245 | A | 12/2000 | Meriwether et al. |
| 6,379,385 | B1 * | 4/2002 | Kalas et al. ................. 623/17.11 |
| 6,458,158 | B1 | 10/2002 | Anderson et al. |
| 6,558,424 | B2 | 5/2003 | Thalgott |
| 6,638,310 | B2 * | 10/2003 | Lin et al. .................... 623/17.11 |
| 6,696,073 | B2 | 2/2004 | Boyce et al. |
| 6,730,125 | B1 | 5/2004 | Lin |
| 6,761,739 | B2 | 7/2004 | Shepard |
| 6,855,166 | B2 | 2/2005 | Kohrs |
| 6,855,167 | B2 | 2/2005 | Shimp et al. |
| 6,896,701 | B2 | 5/2005 | Boyd et al. |
| 6,902,578 | B1 | 6/2005 | Anderson et al. |
| 6,905,512 | B2 | 6/2005 | Paes et al. |
| 6,986,788 | B2 | 1/2006 | Paul et al. |
| 7,018,412 | B2 | 3/2006 | Ferreira et al. |
| 7,037,339 | B2 | 5/2006 | Houfburg |
| 7,044,968 | B1 | 5/2006 | Yaccarino, III et al. |
| 7,077,866 | B2 * | 7/2006 | Gresser et al. ............. 623/17.16 |
| 7,087,082 | B2 * | 8/2006 | Paul et al. .................. 623/17.11 |
| 7,087,087 | B2 | 8/2006 | Boyer, II et al. |
| 7,115,146 | B2 * | 10/2006 | Boyer et al. ................ 623/23.63 |
| 7,115,222 | B2 * | 10/2006 | Lin et al. .......................... 264/42 |
| 7,226,482 | B2 | 6/2007 | Messerli et al. |

(Continued)

FOREIGN PATENT DOCUMENTS

WO    WO 2005063151 A1 *   7/2005

*Primary Examiner* — Nicholas Woodall
(74) *Attorney, Agent, or Firm* — Sorell Lenna & Schmidt LLP

(57) ABSTRACT

The present invention is an osteoimplant that comprises two or more portions, wherein two or more of the portions are self-interlockable with one another to form the desired osteoimplant. The components of the osteoimplant may be of the same material or of different materials. Suitable materials may include cortical bone, cancellous bone, structural polymer, other biomaterial, or any combination thereof.

20 Claims, 30 Drawing Sheets

(56) References Cited

U.S. PATENT DOCUMENTS

| | | |
|---|---|---|
| 7,267,690 B2 | 9/2007 | Felt |
| 7,323,011 B2 * | 1/2008 | Shepard et al. ............ 623/17.11 |
| 2003/0060825 A1 | 3/2003 | Alfaro et al. |
| 2003/0135275 A1 | 7/2003 | Garcia et al. |
| 2003/0181979 A1 * | 9/2003 | Ferree ........................ 623/17.11 |
| 2004/0078078 A1 | 4/2004 | Shepard |
| 2005/0251267 A1 * | 11/2005 | Winterbottom et al. ... 623/23.63 |
| 2006/0195191 A1 | 8/2006 | Sweeney, II et al. |
| 2007/0055377 A1 | 3/2007 | Hanson et al. |
| 2009/0036997 A1 * | 2/2009 | Bayon et al. ................ 623/23.75 |
| 2011/0195052 A1 * | 8/2011 | Behnam et al. .............. 424/93.6 |

* cited by examiner

Cross-section view of possible graft

MULTIPLE COMPONENT OSTEOIMPLANT

CROSS-REFERENCE TO RELATED APPLICATIONS

This application claims benefit of U.S. Provisional Application No. 60/955,837 filed on Aug. 14, 2007, and U.S. Provisional Application No. 60/980,291 filed on Oct. 16, 2007, the contents of each of which are incorporated herein in their entirety.

FIELD OF THE INVENTION

The present disclosure relates to apparatus and methods for multiple component osteoimplants. More particularly, the present disclosure relates to apparatus and methods for multiple component osteoimplants with interlockable or attachable interfaces.

BACKGROUND OF THE INVENTION

The present invention relates to apparatus and methods for assembling a combination bone implant or intervertebral spacer for encouraging bony healing or attachment, including intervertebral fusion, that substantially decreases or eliminates the possibility of the implant coming apart prior to implantation. The apparatus of the present invention may offer benefits associated with different materials.

A desirable characteristic of many bone implant devices is that the implant can stimulate bone growth or become integrated into the adjacent bone structures of the body in the area of the implant. Cancellous bone, Allograft bone-containing composite materials such as Plexur™ manufactured by Osteotech®, Inc., or other osteoinductive or osteoconductive material(s), for example, can provide a tissue penetration or fusion component to an implant. That is, cancellous bone, Plexur™, or other osteoinductive or osteoconductive material(s), can be suitable to assist bone growth or bone regeneration.

Another desirable characteristic of many bone implant devices is that the implant provide strength and support. Cortical bone or other suitable structural polymer, for example, may provide a load bearing component to an implant.

There is a need in the art for apparatus and methods for multiple component osteoimplants. There is a further need in the art for apparatus and methods for multiple component osteoimplants with interlockable or attachable interfaces to increase the ease of assembly and use, particularly in or near the operating room. There is a further need in the art for apparatus and methods for multiple component osteoimplants having a tissue penetration or fusion component and a load bearing component, providing the benefits of each component in a single implant.

BRIEF SUMMARY OF THE INVENTION

In one embodiment, the present disclosure relates to a multiple component osteoimplant. The multiple component osteoimplants may comprise interlockable interfaces between two or more of the multiple components.

In another embodiment, the present disclosure relates to an osteoimplant comprising two or more bone portions, wherein two or more of the bone portions are self-interlockable with one another to form the desired osteoimplant.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying Figures, in which:

DEFINITIONS

Figure 1:
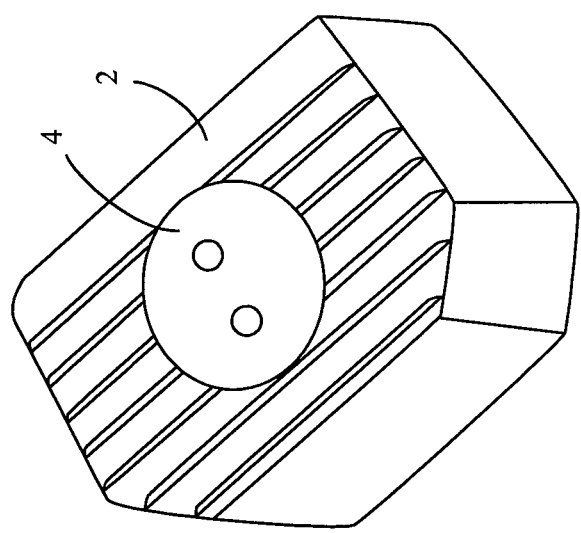
FIG. 1 is several views of an implant having a threaded dowel in accordance with an embodiment of the present invention.
Figure 1:
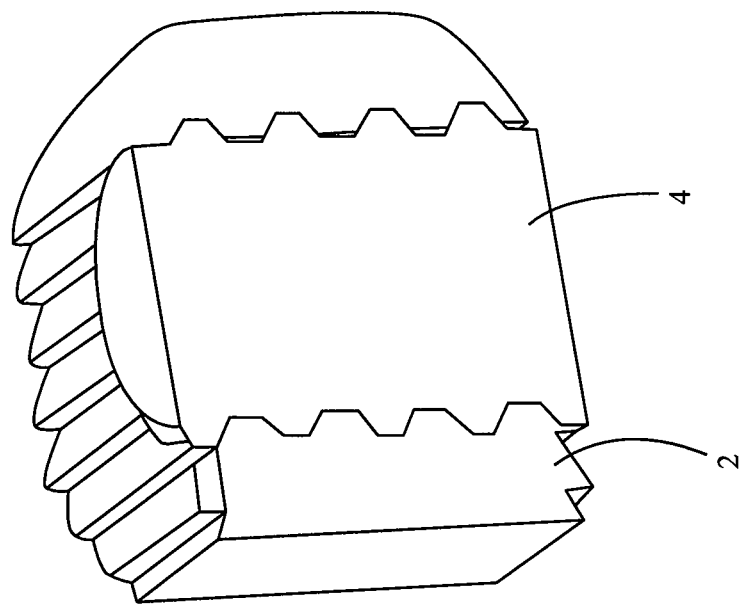

The term "biocompatible", as used herein, is intended to describe materials that, upon administration in vivo, do not induce undesirable side effects. The material preferably does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

"Demineralized" is used to refer to bone-derived material that have been subjected to a process that causes a decrease in the original mineral content. The phrase "partially demineralized" as applied to bone refers to bone possessing from about 8% to about 90% by weight of its original inorganic mineral content, and the phrase "fully demineralized" as applied to bone refers to bone possessing less than about 8% by weight, for example, less than about 1% by weight, of its original inorganic mineral content. The unmodified term "demineralized" as applied to bone is intended to cover any one or combination of the foregoing types of demineralized bone.

The term "osteoconductive", as used herein, refers to the ability of a substance or material to provide surfaces which are receptive to the growth of new bone.

The term "osteogenic" refers to the ability of a substance or material that can induce bone formation.

"Osteoinductive", as used herein, refers to the quality of being able to recruit cells (e.g., osteoblasts) from the host that have the potential to stimulate new bone formation. In general, osteoinductive materials are capable of inducing heterotopic ossification, that is, bone formation in extraskeletal soft tissues (e.g., muscle).

The term "plasticizer", as used herein, refers to an additive that softens hard polymers or plastics. The plasticizer makes the polymer formable or flexible. Plasticizers are thought to work by embedding themselves between the chains of polymers, spacing them apart, and thus lowering the glass transition temperature. Preferably, the plasticizers used in the inventive osteoimplant are non-toxic and biocompatible.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as RNAi, siRNA, or shRNA.

As used herein, a "polypeptide", "peptide", or "protein" includes a string of at least three amino acids linked together by peptide bonds. The terms "polypeptide", "peptide", and "protein", may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide", as used herein, refer to any polymer or oligomer of carbohydrate residues. The polymer or oligomer may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen" refers to a chemical compound that may be part of the osteoimplant and upon implantation or prior to implantation diffuses, dissolves, and/or degrades to leave a pore in the osteoimplant. The porogen may be introduced into the osteoimplant during manufacture, during preparation of the osteoimplant (e.g., in the operating room), or after implantation. The porogen essentially reserves space in the osteoimplant, but once the osteoimplant is implanted, the porogen diffuses, dissolves, or degrades, thereby inducing porosity into the osteoimplant. In this way the porogen provides latent pores. In certain embodiments, the porogen may also be leached out of the osteoimplant before implantation. This resulting porosity of the osteoimplant generated during manufacture or after implantation (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogen can also be natural or synthetic polymers, oligomers, or monomers that are water soluble or degrade quickly under physiological conditions. Exemplary polymers include polyethylene glycol, poly(vinylpyrrollidone), pullulan, poly(glycolide), poly(lactide), poly(lactide-co-glycolide), other polyesters, and starches.

The term "porosity" refers to the average amount of nonsolid space contained in a material (e.g., a composite of the present invention). The porosity of a composite can be defined as the ratio of the total volume of the pores (i.e., void volume) in the material to the overall volume of the composite. Porosity may in certain embodiments refer to "latent porosity" wherein pores are only formed upon diffusion, dissolution, or degradation of a material occupying the pores. The pores in such an instance may be formed after implantation.

DETAILED DESCRIPTION

The present disclosure relates to apparatus and methods for multiple component osteoimplants for encouraging bony healing or attachment, including intervertebral fusion. At some times the description may refer to the implant as comprising two or more combined portions. The term "combined" is not intended to be limiting, and encompasses coupling, interfacing, and other mechanical, chemical, and other means of connecting two or more components. More particularly, the present disclosure relates to apparatus and methods for multiple component osteoimplants with interlockable interfaces. The applications of such devices may be optimized for use in, for example but not limited to, cervical, thoracic, or lumbar regions of the spine, or in other musculoskeletal applications. In one embodiment, the implant of the present disclosure may comprise two or more components. The components may be of the same material or of different materials. Materials may include cortical bone, cancellous bone, structural polymer, other biomaterial, or any combination thereof.

In certain embodiments, the osteoimplant or composite of the osteoimplant may include particles of bone-derived material. The bone-derived material of such composites may include one or more of nondemineralized bone particles, sections or pieces, demineralized bone particles, sections or pieces, lightly demineralized bone particles, sections or pieces, and deorganified bone particles, sections or pieces. The bone-derived material may include one or more of cortical bone, cancellous bone, and cortico-cancellous bone. Also, the bone-derived material may include autogenous bone, allogenic bone, and xenogeneic bone. In certain embodiments, the composite includes an inorganic material and/or a bone substitute material. Exemplary inorganic materials or bone substitute materials useful in the inventive composites include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, BIOGLASS™, fluorapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium, sodium, potassium, etc.), and combinations and derivatives thereof. In certain embodiments, the particles themselves are composites that include one or more of an inorganic material, a bone substitute material, and a bone-derived material; and one or more of bovine serum albumin, collagen, an extracellular matrix component, a synthetic polymer, and a natural polymer. The composite may range from approximately 10% particles to about 95% particles by weight, for example, approximately 50% particles to approximately 80% particles by weight. In certain embodiments, the composite is approximately 50%, approximately 55%, approximately 60%, or approximately 65% particles by weight. The composite may also include other components. For example, the composite may further include one or more of an initiator, accelerator, catalyst, solvent, wetting agent, lubricating agent, labeling agent, plasticizer, radiopacifier, porogen, bioactive agent, biostatic agent, cell, polynucleotide, protein (e.g., bone morphogenic protein, cytokine, growth factor, aniogenic factor), pharmaceutical agent (e.g., anti-inflammatory agent, analgesic, antibiotic, etc.), and pharmaceutically acceptable excipient. In certain embodiments, the composite includes a plasticizer that softens the composite making it more pliable. Exemplary plasticizer include glycerol and poly(ethylene glycol) (PEG) (e.g., PEG 8000, PEG 6000, PEG 4000). In certain embodiments, the polymer component of the composite includes PEG blended, grafted, or co-polymerized with the polymer. In certain embodiments, the composite includes a porogen that diffuses, dissolves, and/or degrades after implantation of the composite leaving a pore. The porogen may be a gas (e.g., carbon dioxide, nitrogen), liquid (e.g., water), or solid (e.g., crystalline salt). The porogen may be a water-soluble chemical compound such as a carbohydrate (e.g., poly(dextrose), dextran), salt, polymer (e.g., polyvinyl pyrrolidone), protein (e.g., gelatin), pharmaceutical agent (e.g., antibiotics), small molecule, etc. A polymer used in preparing the implant may be selected from monomers, pre-polymers, oligomers, polymers, cross-linked polymers, partially polymerized polymers, partially cross-linked polymers, or any combinations thereof. For example, the implant may include monomers, oligomers, and polymers. Exemplary polymers useful in the implant may include, but are not limited to, poly(lactide), poly(glycolide), poly(lactide-co-glycolide), poly(D,L-lactide-co-glycolide), poly(L-lactide-co-glycolide), poly(caprolactone), polyurethane, polycarbonates, polyarylates, poly(propylene fumarates), polyphosphazines, or combinations, blends, or co-polymers thereof. Some of these polymeric materials may be combined with allograft bone to provide one or more of the components of the implant. Porosity may be added, as with a porogen, or $CO_2$ treatment. The bone/polymer material may be used to create load-resistant components, tissue-penetrated components or both. In a further embodiment, at least one load-bearing material may be incorporated in the implant to fulfill any structural requirements of the implant. The components of the present invention can be joined, compressed, or attached particles, or pieces or sections of any or a combination of the above.

A characteristic of one embodiment of the osteoimplant of the present disclosure is that the implant may stimulate bone growth or become integrated into the adjacent bone structures of the body in the area of the implant. Cancellous bone, Plexur™, or other osteoinductive or osteoconductive material(s), such as some of the materials listed above, may provide a tissue penetration or fusion component to an implant and may be suitable for adequate bone growth or bone regeneration in the area of the implant. Cancellous bone used in the osteoimplant may be osteoconductive, osteoinductive, or treated to provide or increase osteoinductivity. Another characteristic of one embodiment of the osteoimplant of the present disclosure is that the implant may provide strength and support for the surrounding area of the implant. Cortical bone or other suitable structural polymer or material, such as some of the materials listed above, may provide a load bearing or load resisting component to an implant.

In some embodiments, the tissue penetration or fusion component may be partially or fully load-bearing. Similarly, in some embodiments, the load bearing component may be penetrated and/or remodeled. Generally, an osteoimplant of the present disclosure may support some load of the skeletal structure in the area of the implant as tissue penetrates and fusion is formed. In a further embodiment, the osteoimplant may share at least a portion of the load with the newly formed tissue. Thus, a multiple component osteoimplant having a tissue penetration or fusion component and a load bearing component may provide the benefits and advantages of each component in a single implant.

In one embodiment, the implant may have a threaded cancellous piece surrounded, at least partly, by a cortical piece. The cancellous piece may be of any desired configuration, including a dowel, and the cortical piece may also be of any desired configuration, including a shell. The cancellous dowel may provide the implant with osteoconductive and other desirable biological properties. The cancellous portion also may allow enhanced cellular penetration and encourage early bony bridging between both endplates. The cortical shell portion may provide mechanical strength of the implant. In some embodiments, the cortical shell may provide the majority of the mechanical strength of the implant. The cancellous portion also may provide mechanical strength. The cortical shell may be demineralized on the superior and inferior surfaces, which may further provide osteoinductive properties to the implant. In further embodiments, some form of demineralized bone matrix composition may be injected into the cancellous portion of the implant, which may also enhance the osteoinductivity of the implant. The cortical bone may or may not include ridged or roughened superior and/or inferior surfaces for helping the implant resist motion, dislocation, or expulsion. The cancellous and/or cortical bone may be treated to impart desired biological properties, including drug delivery, osteoinductivity, etc. In some embodiments, one component may be configured so as to resist mechanical loads, and another, interlocking component may be configured to permit or increase cell and tissue through-growth. In some embodiments, the mechanical load-resisting component may be cortical bone and the tissue penetrating component may be cancellous bone. In some embodiments, the tissue penetrating component may be a solid (e.g., substantially non-porous) or open porous bone/polymer composite, such as but not limited to, composites containing bone that are porous (e.g. Plexur® P, Osteotech Inc., Eatontown, N.J.) or non-porous, including those identified in U.S. Pat. No. 6,696,073, incorporated herein by reference.

In one embodiment, threading may be used to greatly minimize the chance or likelihood that portions of a combination implant may come apart. For example, two portions of a combination implant as described herein may be threadingly engaged. In one embodiment, as illustrated in FIG. 1, the two portions may comprise a cancellous portion and a cortical portion. The threading mechanism may maintain the components in a fixed position in relation to each other without requiring the tight fit that is ordinarily required for other types of combination implants. The threaded components may be oriented in any direction with respect to the planes of the implant. The threaded dowel is later machined, so that it is no longer a dowel in the final view.

Figure 2B:
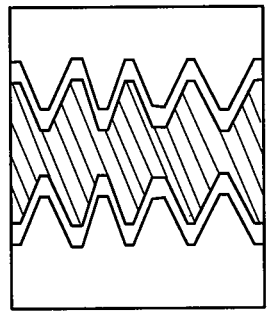
FIG. 2 is cross-sectional views of an implant having a threaded dowel in accordance with an embodiment of the present invention.
Figure 2A:
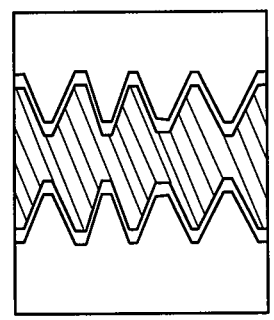

In a further embodiment, the implant may comprise a cortical shell 2 containing a central bore for receiving a cancellous dowel 4. The cortical shell 2 may have a primary load-bearing direction generally in line with the vertical direction of the spine. The central bore may be drilled and tapped with threads, and the cancellous dowel 4 may be threaded. The threads of the central bore correspond with the threads of the cancellous dowel 4. The cancellous dowel 4 may be a dowel similar to the Graftech® Cervical Dowel manufactured by Osteotech®, Inc., located in Eatontown, N.J. The cancellous dowel may not need to be machined along the primary load-bearing direction. In some embodiments, the cortical shell 2 may provide most of the structural support for the implant while the cancellous bone portion 4 may provide most of the osteoconductive properties of the implant. In another embodiment, the osteoimplant may take the form of a dowel-in-dowel formulation, including a cortical dowel, which may have an intermedullary canal which itself may be threaded with a corresponding plug that may be threaded. In some embodiments, the threads may be coarse. However, it is recognized that any variation of threading may be used from very fine threads to very coarse threads. Also, the threads may have any suitable pitch may be used for allowing the bone portions to remain held together without the need for being precisely machined. For example, FIG. 2A illustrates an embodiment of the implant having generally coarse, tightly fitting threads. FIG. 2B illustrates bone portions that are not as precisely machined, but the bone portions remain held together due to the threads. In further embodiments, the threads may be continuous or discontinuous. When assembled, the cancellous dowel 4 may span the entire height of the implant, such that the cancellous dowel 4 may make contact with superior and inferior endplates of the vertebrae. The cancellous bone portion may traverse the height of the implant so as to provide a direct and uninterrupted route for the growth and attachment of new bone cells and vasculature.

It is to be expressly understood that each of the components of the osteoimplant of the present invention may be any of the materials listed above. For example, with reference to FIG. 1, the outer portion (identified as 2) may be cancellous bone, and the inner portion (identified as 4) may be cortical bone; or the outer portion may be cortical bone, and the inner portion may be cancellous bone; or the outer portion may be a polymer, and the inner portion either cancellous or cortical bone; or the outer portion may be either cancellous or cortical bone, and the inner portion may be a polymer; or the various components may be combinations of the above materials. Other materials and combinations of materials also may be used. Furthermore, with reference to each of the Figures and embodiments described herein, while reference may be made to one segment being cortical bone and another segment being cancellous bone, it is to be recognized that the sources of material may be reversed, as described above in this paragraph, and other and combinations of materials may be used, also as described in this paragraph. Thus, the combinations of this paragraph should be read in combination with each Figure and embodiment of this disclosure, as if it were fully repeated for each.

Figure 3:
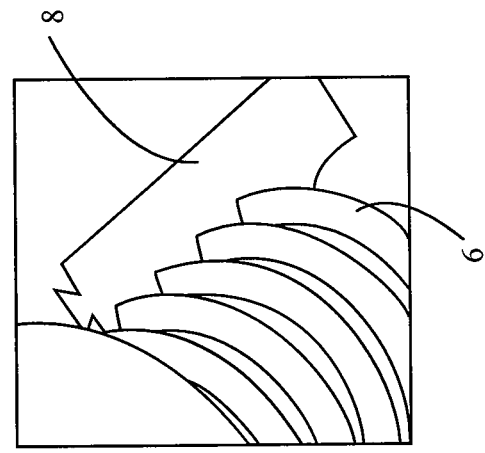
FIG. 3 is several views of an implant having a threaded dowel in accordance with another embodiment of the present invention.
Figure 3:
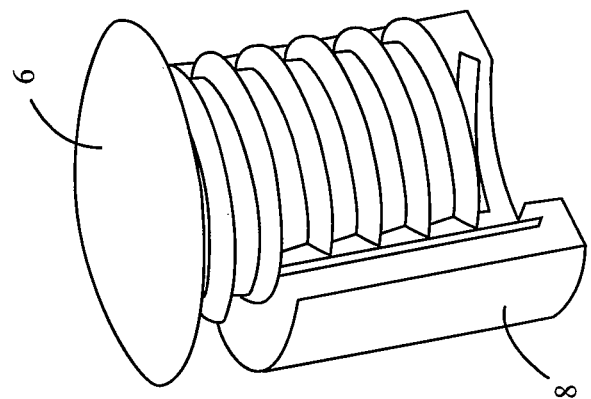
Figure 3:
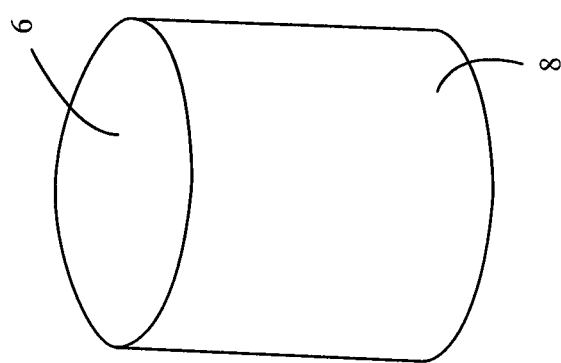

In a further embodiment, illustrated in FIG. 3, the dowel 6 may comprise a head and be generally shaped like a screw. The cortical bone portion 8 may be generally cylindrical comprising a center bore to receive the screw shaped dowel 6. In other embodiments, the cortical bone portion 8 may be any shape, including square, rectangular, polygonal, etc. In one embodiment, the dowel head may mate with a top surface of the cortical bone portion such that the dowel head forms the entire top surface of the implant. In other embodiments, the dowel head may form only a portion of the top surface of the implant. Although illustrated as a domed-shaped head in FIG. 3, the head may be any shape including square, rectangular, polygonal, etc. In some embodiments, the cortical bone portion 8 may comprise more than one piece. For example, the cortical bone portion 8 may be formed from two, three, four, or more pieces. The cortical bone pieces may mate together using dovetail joints. However, it is recognized that any other suitable joint may be used to join the cortical bone pieces to form the cortical bone portion 8.

Figure 4:
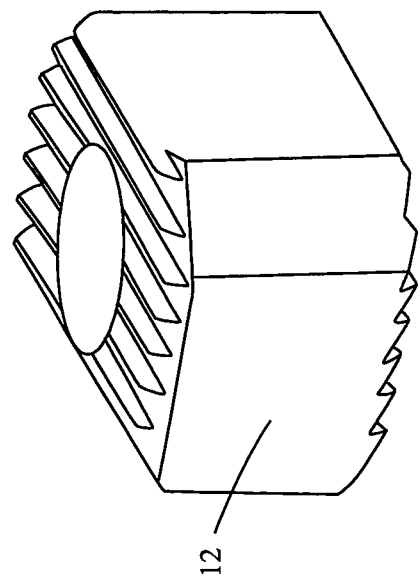
FIG. 4 is several views of an implant having a threaded dowel in accordance with a further embodiment of the present invention.
Figure 4:
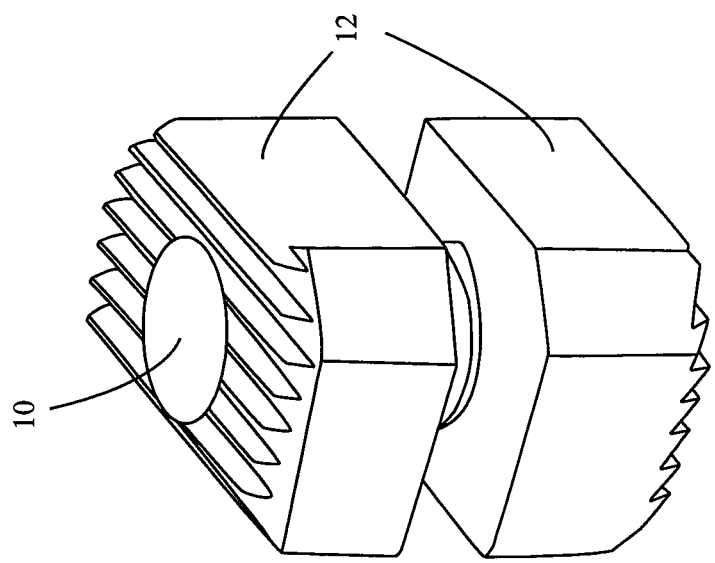

In another embodiment, the implant may comprise more than two portions. For example, FIG. 4 illustrates an implant including a cancellous dowel 10 and multiple pieces of cortical bone 12. Specifically, in FIG. 4, two cortical bone portions 12 are illustrated. However, it is recognized that any suitable number of cortical bone portions may be used in the implant of the present disclosure, including three cortical bone portions, four cortical bone portions, five cortical bone portions, or more. The cancellous dowel 10 may be used to retain the multiple pieces of cortical bone together. The cancellous dowel 10 may be threaded and central bores of the cortical bone portions 12 may be drilled and tapped to receive the threaded dowel.

Figure 5:
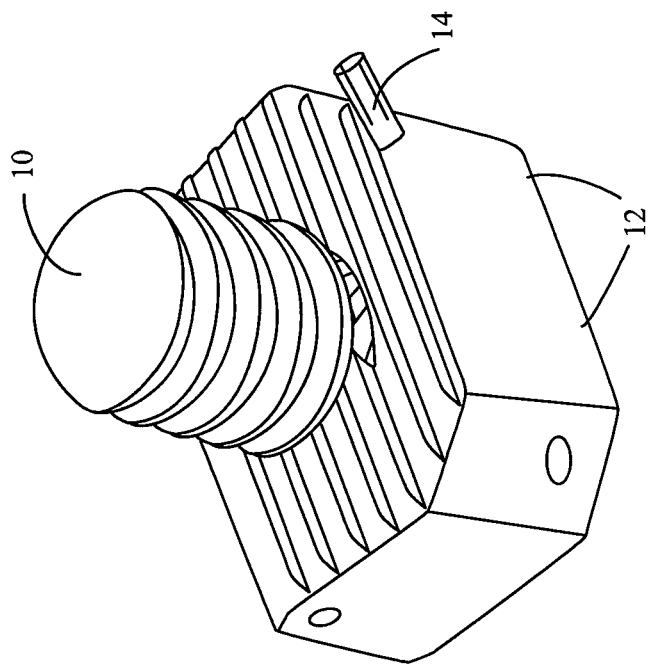
FIG. 5 is several views of an implant having a threaded dowel in accordance with yet another embodiment of the present invention.
Figure 5:
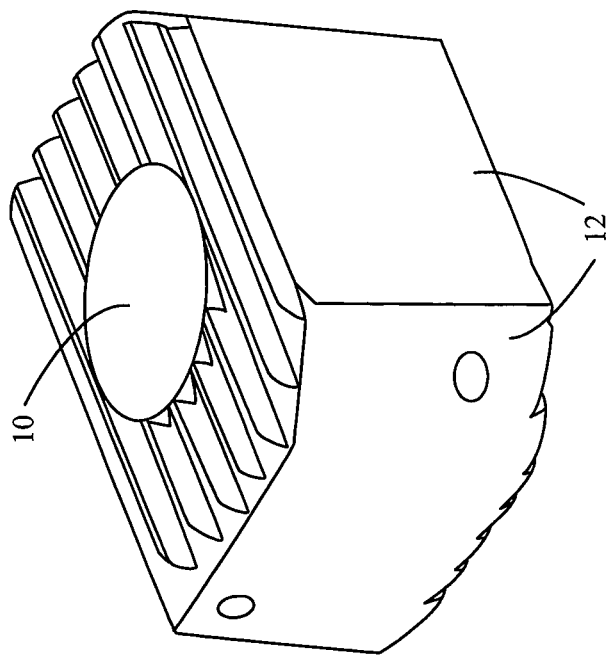

As shown in FIG. 4, the cortical bone portions 12 may be stacked in a direction that is generally in line with the vertical direction of the spine. In an alternative embodiment, the cortical bone portions 12 may be aligned, or stacked, in a direction that is not in line with the vertical direction of the spine. As illustrated in FIG. 5, the cortical bone portions 12 may be aligned in a direction that is generally orthogonal to the vertical direction of the spine. The cortical bone portions 12 may be pinned together, for example, using bone pins 14, such as cortical bone pins. The cortical bone portions 12 may be drilled and tapped with threads as if they were a single piece of cortical bone. The cortical bone portions 12 may be temporarily clamped together during drilling and tapping. A cancellous dowel 10 may be threaded and received within the bore of the cortical pieces 12. The cortical bone portions 12 may remain temporarily clamped while the dowel 10 is screwed into the implant. As stated previously, the threads of the central bore correspond with the threads of the cancellous dowel 10. The cancellous dowel 10 may be a dowel similar to the Graftech® Cervical Dowel manufactured by Osteotech®, Inc. In some embodiments, the threads may be coarse. However, it is recognized that any variation of threading may be used from very fine threads to very coarse threads. Similarly, the threads may be continuous or discontinuous.

Figure 6:
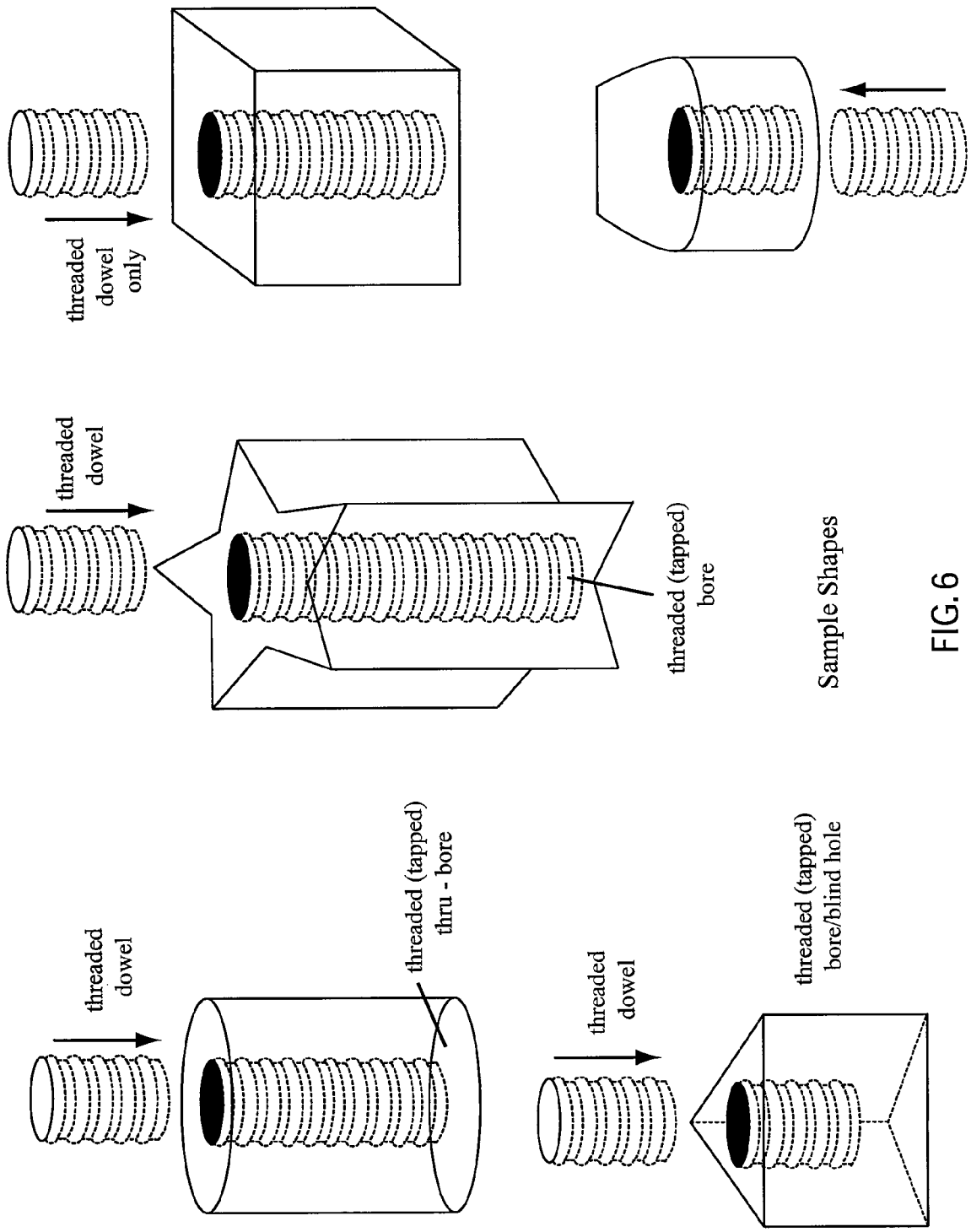
FIG. 6 is several views of an implant having a threaded dowel in accordance with another embodiment of the present invention.

The cortical bone portion(s) may form any suitable shape or configuration, as illustrated in some examples in FIG. 6. Furthermore, although described with respect to cortical bone portions and cancellous bone portions, threads may be used to combine and/or hold two or more portions of an implant together, regardless of the effects of freeze-drying, transportation, etc. For example, two or more portions of cortical bone may be combined, two or more portions of cancellous bone may be combined, one or more portions of cortical bone may be combined with one or more portions of cancellous bone, two or more polymers may be combined, one or more polymers may be combined with one or more bone portions, or any other suitable bone/polymer combination may be formed. Any biologic or biocompatible material may be used for any of the portions.

Figure 7:
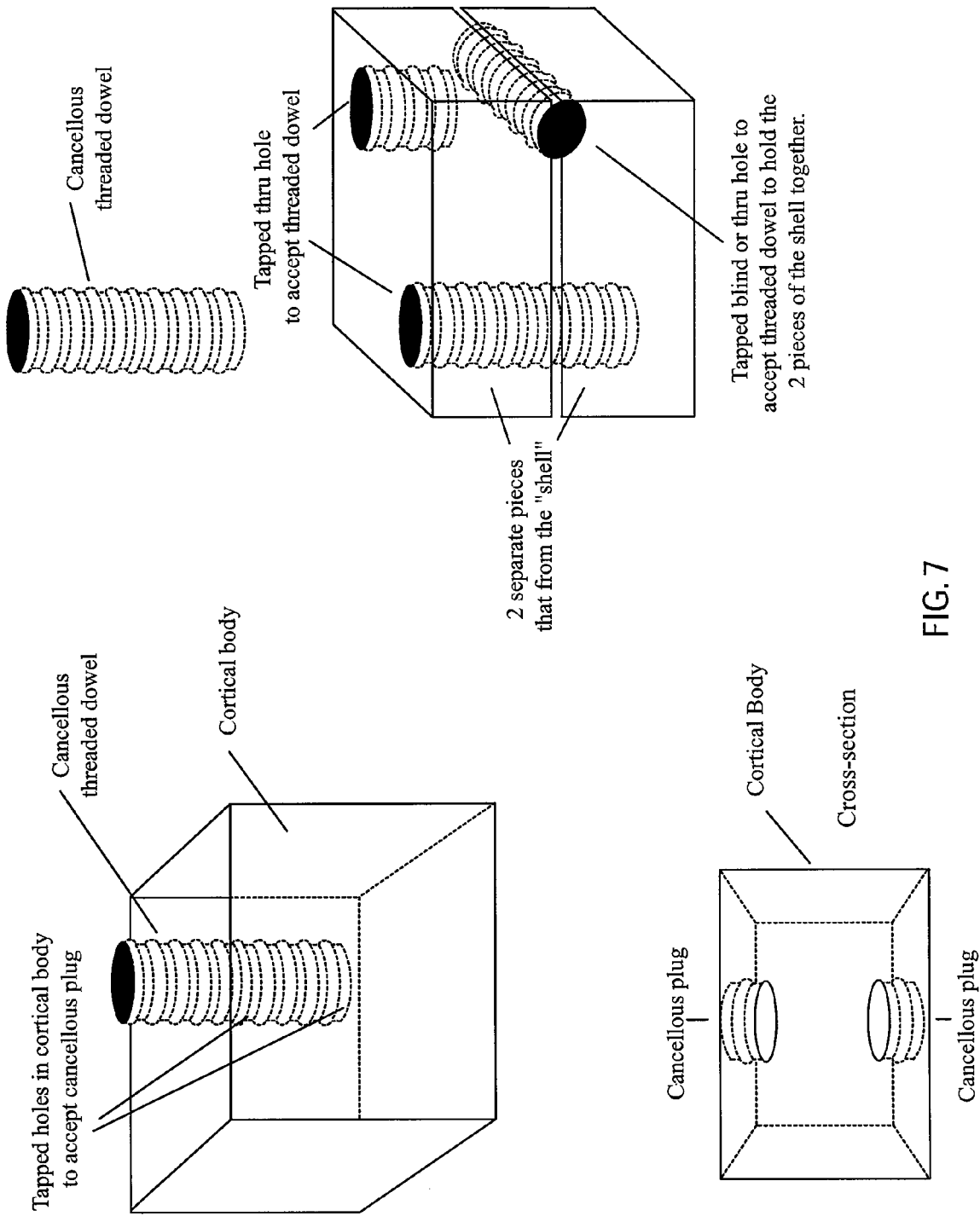
FIG. 7 is several views of an implant having a threaded dowel in accordance with an even further embodiment of the present invention.

In yet a further embodiment, as illustrated in FIG. 7, the cancellous dowel need not go all the way through the cortical bone portion, from one surface to another. That is, a cortical block may have top and bottom surfaces drilled and tapped to a particular depth, but not all the way through, e.g., a blind hole. As such, a threaded bone portion, such as a threaded cancellous bone portion, may be threaded into each of the top and bottom surfaces. This may allow faster implant incorporation than an implant comprising cortical bone alone by providing the implant with osteoinductive properties at the superior and inferior surfaces. This also provides a cavity to place a growth-enhancing or an inductive material, such as members of the Grafton® DBM family of forms from Osteotech®, Inc. Similarly, an implant as described herein may provide increased strength to the implant and less likelihood of implant subsidence or collapse than would a purely cancellous implant.

In other embodiments, the bore need not be central and may be located anywhere throughout the cortical bone portion(s) or any other material used in place of the cortical bone portion(s). Similarly, more than one bore and dowel may be provided in the cortical bond portion(s). For example, FIG. 7 illustrates a cortical or structural block that incorporates several bores for the reception of several cancellous dowels. Furthermore, the threading is not limited to the grain direction, but the threading may apply in any direction.

Figure 8:
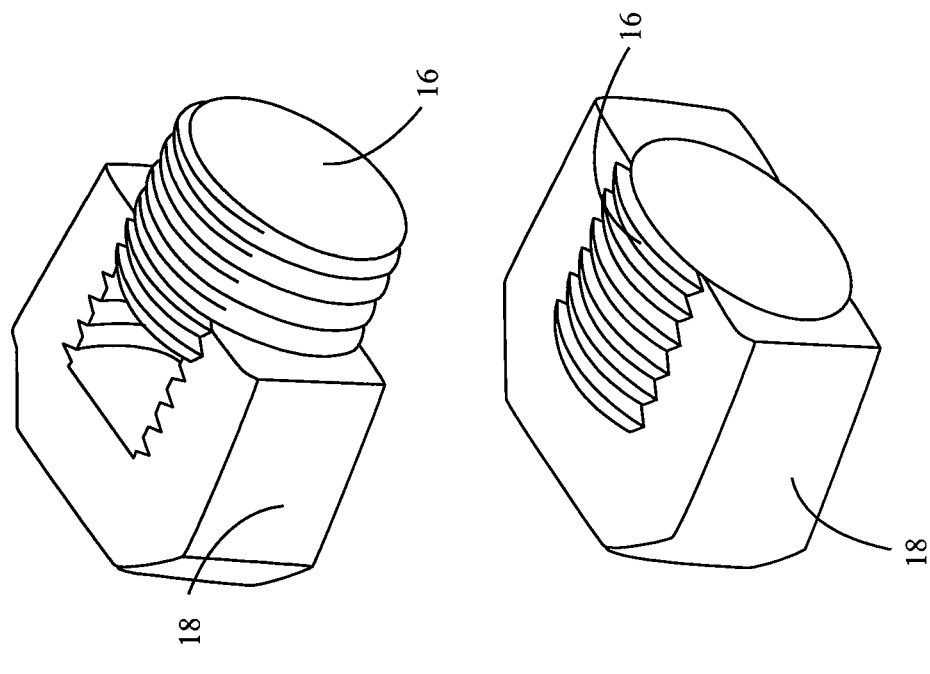
FIG. 8 is several views of an implant having a threaded dowel in accordance with yet another embodiment of the present invention.
Figure 8:
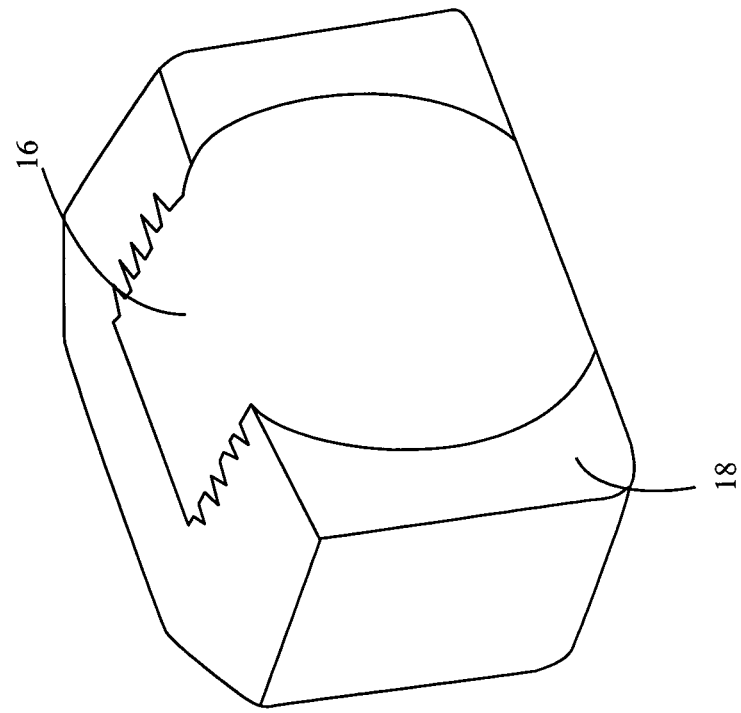

In an alternative embodiment, the cortical or structural portion of the implant may have a cavity directed along the axial plane of the spine. A cancellous dowel 16 may be positioned or threaded within the cavity of the cortical 18 or structural portion of the implant. That is, the cortical bone portion 18 may be threaded on one or more of its sides rather than the top or bottom surfaces, as illustrated in FIG. 8. In such an embodiment, and for the other embodiments disclosed herein, the cortical bone portion 18 does not need to entirely surround the dowel 16. In some embodiments, such as illustrated in FIG. 8, the cortical bone portion may surround the dowel just enough so that the dowel can properly rotate into position and remain in position. As shown in FIG. 8, portions of the dowel that protrude from the top and bottom surfaces of the cortical bone portion 18 may be machined. As a result of this machining, the dowel may assume other configurations, including non-threaded and non-dowel.

The choice of materials for an implant of the present disclosure is not limited to only cortical bone and cancellous bone. Any structural biomaterial or biocomposite that may accommodate a threaded design may be used. Similarly, the Figures are exemplary and use of a threaded mechanism is not limited to the embodiments illustrated in the Figures and described with respect thereto. Any orientation or use of the thread design to assemble multiple pieces of a combination implant may be considered. For example, while in one embodiment, the primary direction of the cortical bone would align with the axial direction of the spine, the cancellous dowel may be oriented at any suitable angle in relation to the axial direction of the spine. The dowel may be oriented in any way within the cortical or structural shell or adjacent to the cortical shell.

Figure 9:
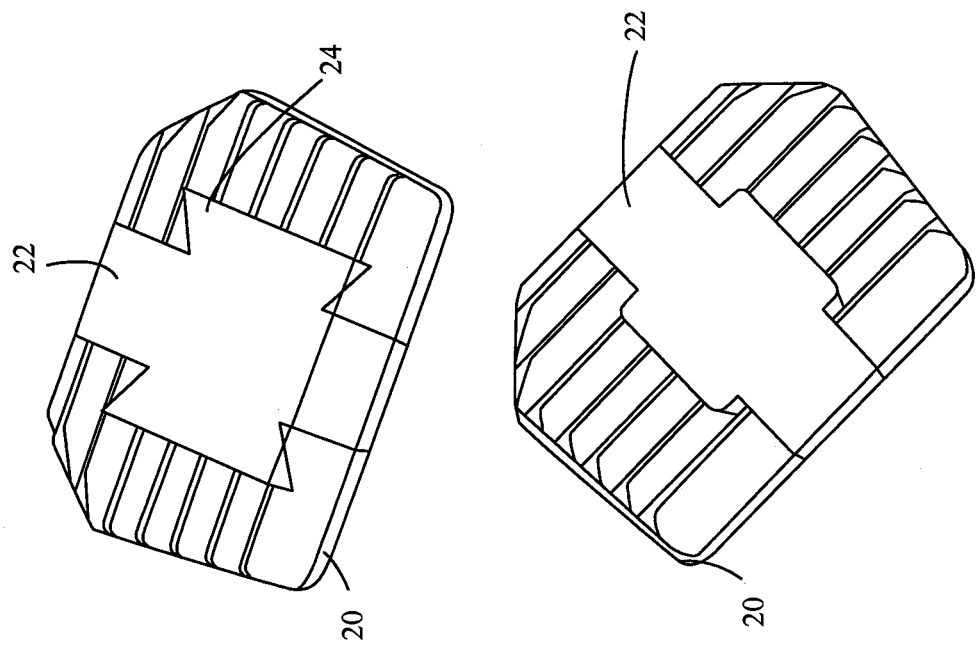
FIG. 9 is several views of an implant having a dovetailed interface in accordance with an embodiment of the present invention.
Figure 9:
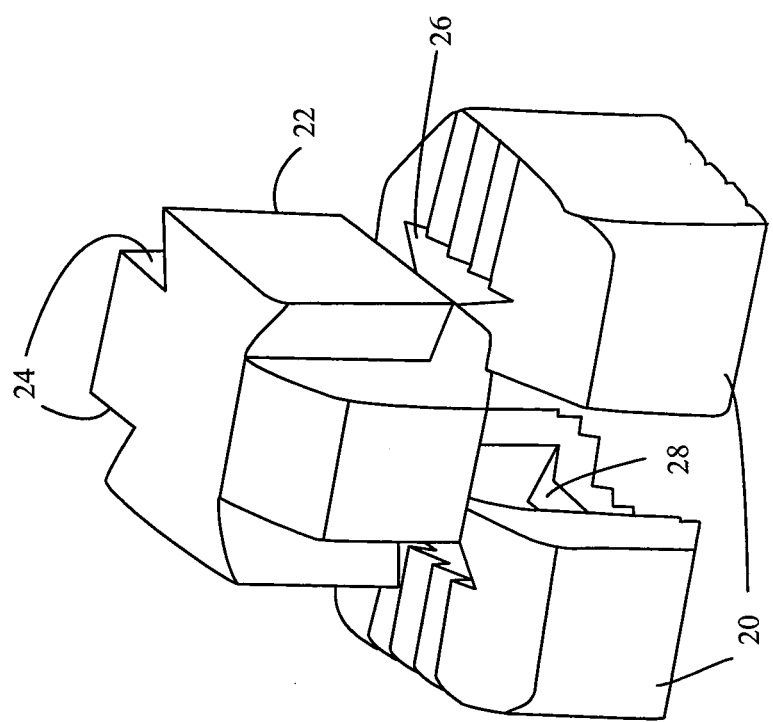

In another embodiment, illustrated in FIG. 9, a dovetail design may be used to combine two or more bone portions to create an implant of the present disclosure. In one embodiment using a dovetail design, two or more cortical bone portions 20 may from the lateral structure of the implant. A cancellous bone portion 22 may form the center of the implant. The cortical bone portions 20 may have dovetail cut-outs 26, which may be generally trapezoidal, for receiving dovetails 24 formed in the cancellous bone portion 22. In a further embodiment, a platform 28 may be formed in the cortical bone portions 20, upon which a portion of the cancellous bone portion 22 may rest. The platform 28 may prevent the cancellous bone portion 22 from slipping through the cortical bone portions 20. However, the cancellous bone portion 22 may remain exposed on both the top and bottom surfaces of the implant.

Figure 10:
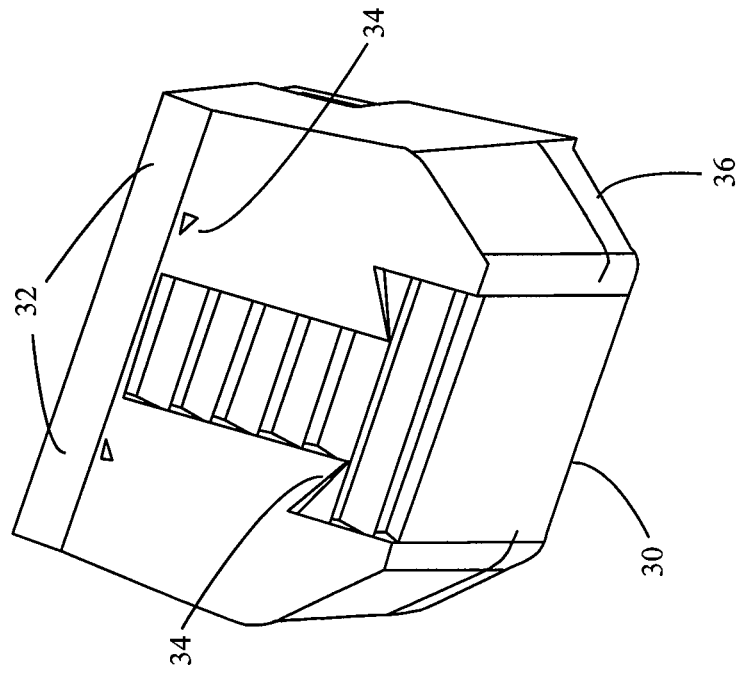
FIG. 10 is several views of an implant having a centered strut in accordance with an embodiment of the present invention.
Figure 10:
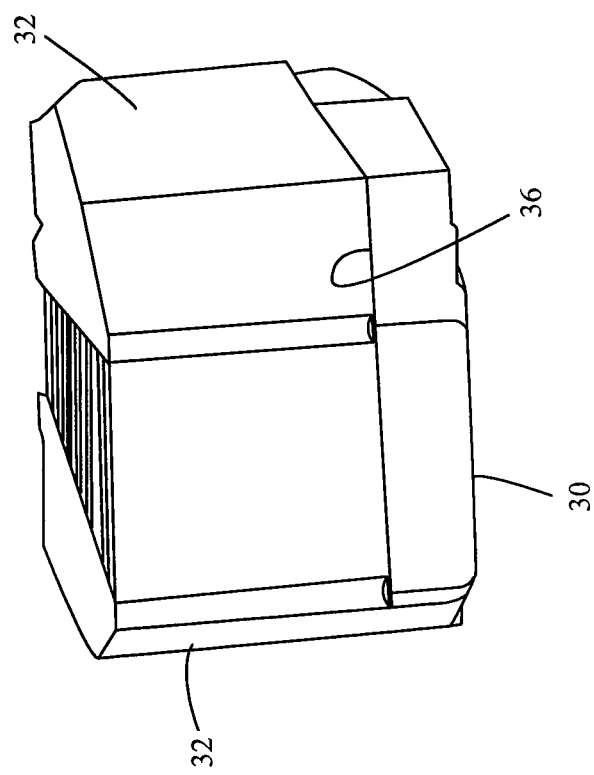

In another embodiment, illustrated in FIG. 10, an implant similar to the dovetailed implant, described above, may comprise a centered cortical bone portion 30 that may further act as the strut or support for the implant. Two or more cancellous bone portions 32 may from the lateral structure of the implant. The centered cortical bone portion 30 may comprise one or more cortical bone pieces. A dovetail design may be used to combine the cancellous bone portions 32 with the centered cortical strut to create an implant of the present disclosure. The cortical bone portion 30 may have dovetail cut-outs, which may be generally trapezoidal, for receiving dovetails 34 formed in the cancellous bone portions 32. In a further embodiment, one or more platforms 36 may be formed in the cortical bone portion 30, upon which a portion of the cancellous bone portions 32 may rest. The platform 36 may prevent the cancellous bone portions 32 from slipping from the cortical bone portion 30. However, the cancellous bone portions may remain exposed on both the top and bottom surfaces of the implant.

Figure 11:
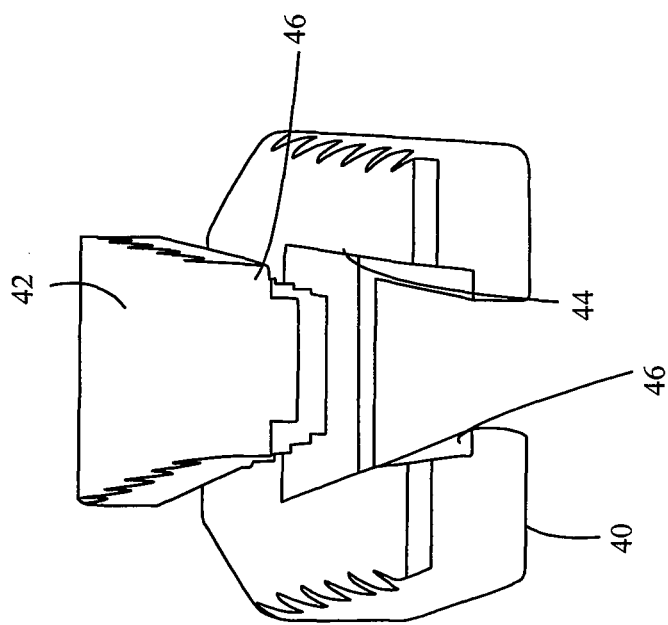
FIG. 11 is several views of an implant having a platform in accordance with an embodiment of the present invention.
Figure 11:
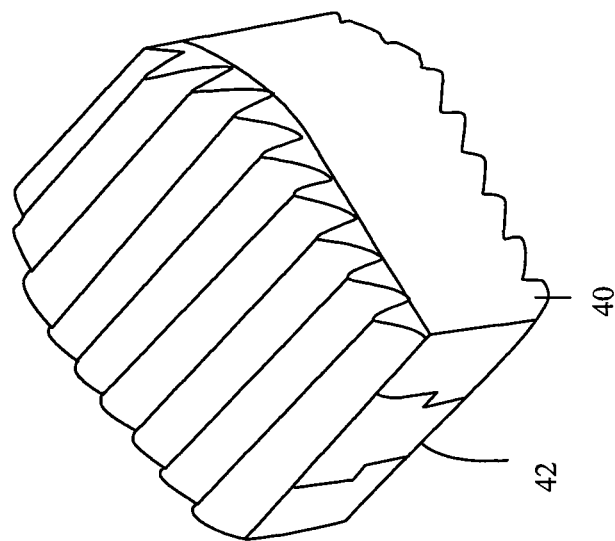

In another embodiment, as illustrated in FIG. 11, an implant of the present disclosure may have an outer shell portion 40 at least partially surrounding a center body portion 42. The shell may be formed of cortical bone or other load-bearing biomaterial, and the body may be formed of cancellous bone or other osteoconductive/osteoinductive material. The cortical shell 40 may be generally U-shaped. In one embodiment, the cortical shell 40 may be U-shaped with a dovetail cut-out 44 forming the inner side of the cortical shell. However, it is recognized that any suitable shape may be used to form the inner side of the U-shaped cortical shell, such as a square, rectangle, triangle, etc. The cut-out may be shaped so that the dovetail is angled just enough to keep the shell 40 and body 42 portions together in the horizontal plane. The cancellous body 42 may fit, or press fit, into the open portion of the U-shaped cortical shell 40. The cortical shell 40 may further comprise a platform 46 upon which a portion of the cancellous body portion 42 may rest. The cancellous body portion 42 may have cut-out 48 at a smaller or thinner end that may rest on the platform 46 of the cortical shell 40. The platform 46 may be located at the bottom of the cortical shell 40. However, it is recognized that the platform 46 may be located at any location of the inner side of the cortical shell 40 between the top and bottom surfaces, and the cut-out 48 on the cancellous body portion 42 may correspond in location with respect to the top and bottom surfaces to that of the location of the platform 46. Thus, the cancellous body portion 42 may be assembled from the top with the cortical shell 40 without falling through the implant. Furthermore, the cancellous body portion 42 may be assembled with the cortical shell 40 so that the cancellous body portion 42 remains exposed on both the top and bottom surfaces of the implant. In one embodiment, the superior and inferior surfaces of the implant may be shaped to conform with the prepared endplates of the vertebral bodies.

In some embodiments, the shape of the shell portion may generally match the anatomical shape of the disc space of the vertebral bodies. For example, the shape of the implant may be similar in shape to the GraftCage® distributed by Osteotech®, Inc. In some embodiments, the shape may be generally trapezoidal. Additionally, the implant may be designed so that it is lordotic. Also, the implant shape may be configured so that the cortical shell portion, or the portion with the more dense tissue, faces anteriorly during implantation. As such, impaction from an inserter or tamping/positioning instrument during implantation will most likely occur at the cortical shell. Also, in some embodiments, the cortical portion may form the dovetail and the cancellous portion may serve as the U-shaped shell. Similarly, the platform may be part of the dovetailed portion while the cut-out portion may be part of the U-shaped portion.

Figure 12:
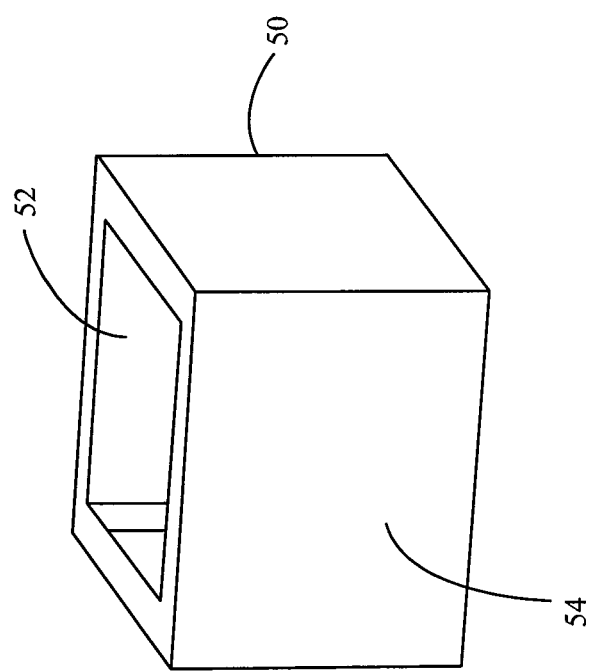
FIG. 12 is several views of an implant having a platform in accordance with another embodiment of the present invention.

In another embodiment of a platform design, illustrated in FIG. 12, an implant of the present disclosure may have an outer shell portion 50 completely surrounding a center body portion 52. The shell 50 may be formed of cortical bone or other load-bearing biomaterial, and the body 52 may be formed of cancellous bone or other osteoconductive/osteoinductive material. The cortical shell 50 may be generally square, rectangular, circular, trapezoidal, polygonal, or any other suitable shape. The cortical shell 50 may have a center portion of the shell open to receive the center body portion 52. The open center portion of the cortical shell 50 may be shaped similar to that of the general shape of the cortical shell, including square, rectangular, circular, trapezoidal, polygonal, or any other suitable shape. The general shape of the open center portion, in some embodiments, may be shaped different than the general shape of the cortical shell. The cancellous body 52 may fit, or press fit, into the open center portion of the cortical shell 50. The cortical shell 50 may further comprise a platform 54 upon which a portion of the cancellous body portion 52 may rest. The cancellous body portion 52 may have cut-out at a smaller or thinner end that rest on the platform of the cortical shell 50. The platform 54 may be located at the bottom of the cortical shell 50. However, it is recognized that the platform 54 may be located at any location of the inner side of the cortical shell 50 between the top and bottom surfaces, and the cut-out on the cancellous body portion 52 may correspond in location with respect to the top and bottom surfaces to that of the location of the platform 54. Thus, the cancellous body portion 52 may be assembled from the top with the cortical shell 50 without falling through the implant. Furthermore, the cancellous body portion 52 may be assembled with the cortical shell 50 so that the cancellous body portion 52 remains exposed on both the top and bottom surfaces of the implant. In one embodiment, the superior and inferior surfaces of the implant may be shaped to conform with the prepared endplates of the vertebral bodies.

Figure 13:
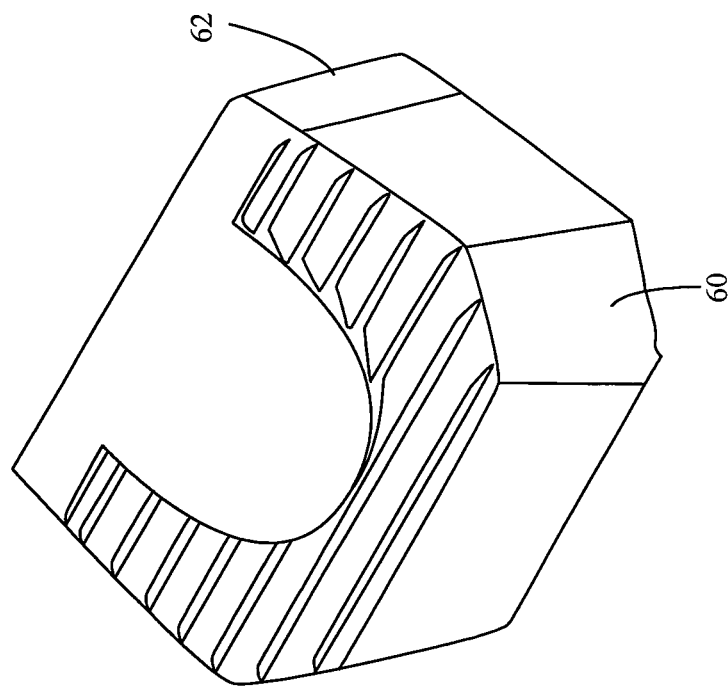
FIG. 13 is several views of an implant having a shelf and channel in accordance with an embodiment of the present invention.
Figure 13:
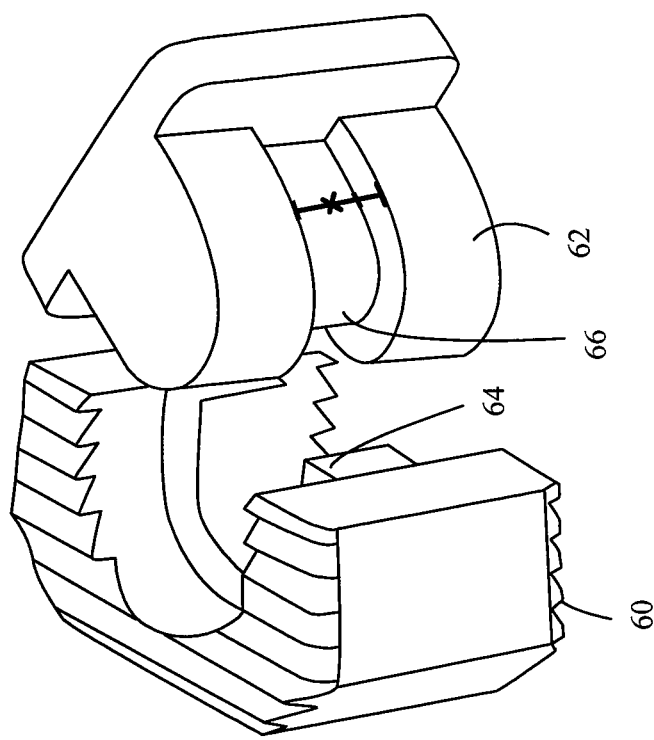

In a further embodiment, illustrated in FIG. 13, a shelved design may be used to combine two bone portions to create an implant of the present disclosure. In one embodiment, a cortical bone portion 60 may be combined with a cancellous bone portion 62 to create the implant. The cortical bone portion 60 may form the anterior portion of the implant. The cancellous bone portion may form the posterior portion of the graft. A "shelf" 64 may be cut from the cortical bone portion to support the cancellous bone portion while still allowing the cancellous bone portion to span the entire implant from top to bottom. The shelf 64 may comprise a generally annular protrusion extending inward from an inner wall of the cortical bone portion 60. The shelf 64 may be located at any position between the top and bottom surfaces of the cortical bone portion 60. In one embodiment, the shelf 64 may be located generally in the center of the inner wall, between the top and bottom surfaces. A "channel" 66 may be cut from the cancellous bone portion 62 corresponding with the shelf 64 of the cortical bone portion 60. In some embodiments, the channel 66 may tightly fit with the shelf 64 of the cortical bone portion 60.

In a further embodiment, the shelf 64 and channel 66 may be cut such that when the implant is freeze-dried, distance "X" may be slightly smaller than distance "Y." The slight variation in distances "X" and "Y" may provide a tight press fit for the cortical and cancellous bone portions.

Figure 14:
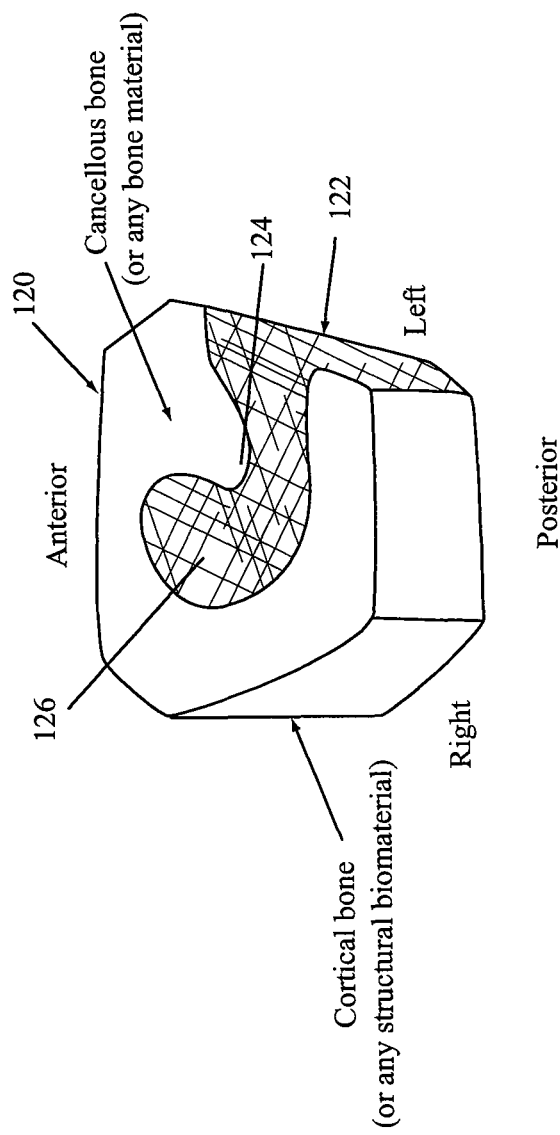
FIG. 14 is several views of an implant having a hook in accordance with an embodiment of the present invention.

In another embodiment, illustrated in FIG. 14, two bone portions 120, 122 may be held together by a "hook" cut-out 124 and corresponding hook 126. As used herein, the term hook may include any protrusion that is more than merely a straight protrusion in one direction. The term hook may include any protrusion that extends in more than one direction. In one embodiment, a portion 120 made from cortical bone or other structural biomaterial may comprise a hook cut-out 124. A portion 122 made from cancellous bone or other biomaterial may comprise a corresponding hook 126. The hook cut-out 124 and corresponding hook 126 can be any size, shape, or configuration so that the hook and cut-out allow the two bone portions 120, 122 to be coupled, such that the two portions do not separate in the medial/lateral direction or the anterior/posterior direction. In further embodiments, the hook cut-out and corresponding hook may be designed such that the two portions do not separate in the superior/inferior direction. In one embodiment, this may be achieved by angulating or curving the hook geometry.

Figure 15:
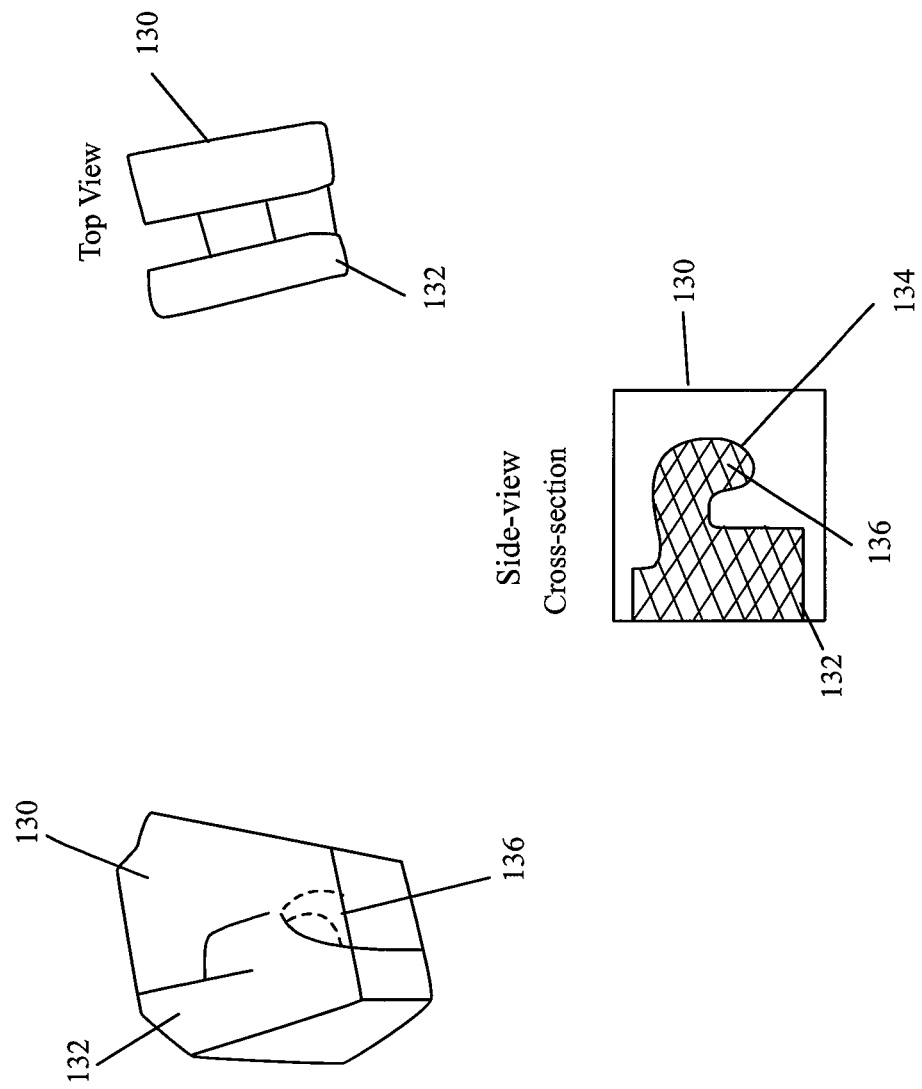
FIG. 15 is several views of an implant having an angulated hook in accordance with an embodiment of the present invention.

Angulating the hook geometry, as shown in FIG. 15, may be described generally as turning the hook cut-out 134 and corresponding hook 136 approximately 90° from the design of FIG. 14. That is, the orientation of the hook may be in the coronal plane rather than the lateral plane. As such, the two bone portions 130, 132 may be coupled, such that the two portions do not separate in the medial/lateral (or posterior/anterior) direction nor the inferior/superior direction. If the hook lies in the center of the implant, and is not exposed when assembled, the implant would be prevented from separating in the posterior/anterior (or medial/lateral) direction as well.

Figure 16:
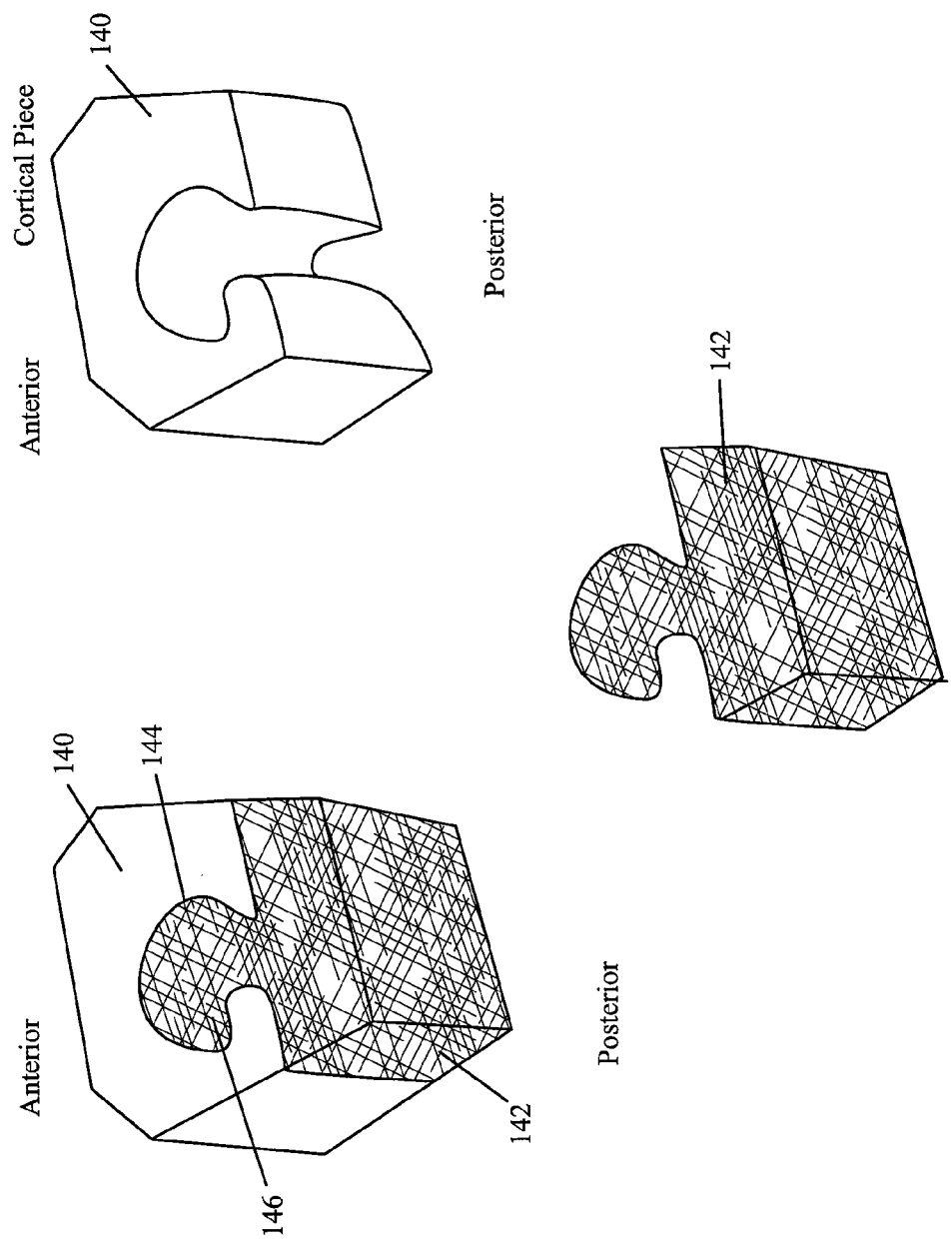
FIG. 16 is several views of an implant having a curved hook in accordance with an embodiment of the present invention.

Curving the hook geometry may be used to retain the two portions so that they do not separate in the medial/lateral direction, the anterior/posterior direction, nor the inferior/superior direction. As illustrated in FIG. 16, the hook cut-out 144 and corresponding hook 146 may be curved in the sagital plane. Thus, the two portions 140, 142 may be prevented from slipping out of the assembled configuration while still maintaining the ability of the implant to be manufactured easily. Although curving has been described with respect to the sagital plane, as with the hook 146, the curvature may be present in any direction or orientation and is not limited to the sagital plane.

Furthermore, although the Figures have been described with the cortical bone portion comprising the hook cut-out and the cancellous bone portion comprising the hook, it is recognized that the hook cut-out and hook can be on either portion. Furthermore, there is no need for either of the components to be structural or osteoconductive. Any biomaterial may be used to produce the implant, including metals, polymers, tissue, etc. Additionally, the implant may be made of more than two portions.

Figure 17:
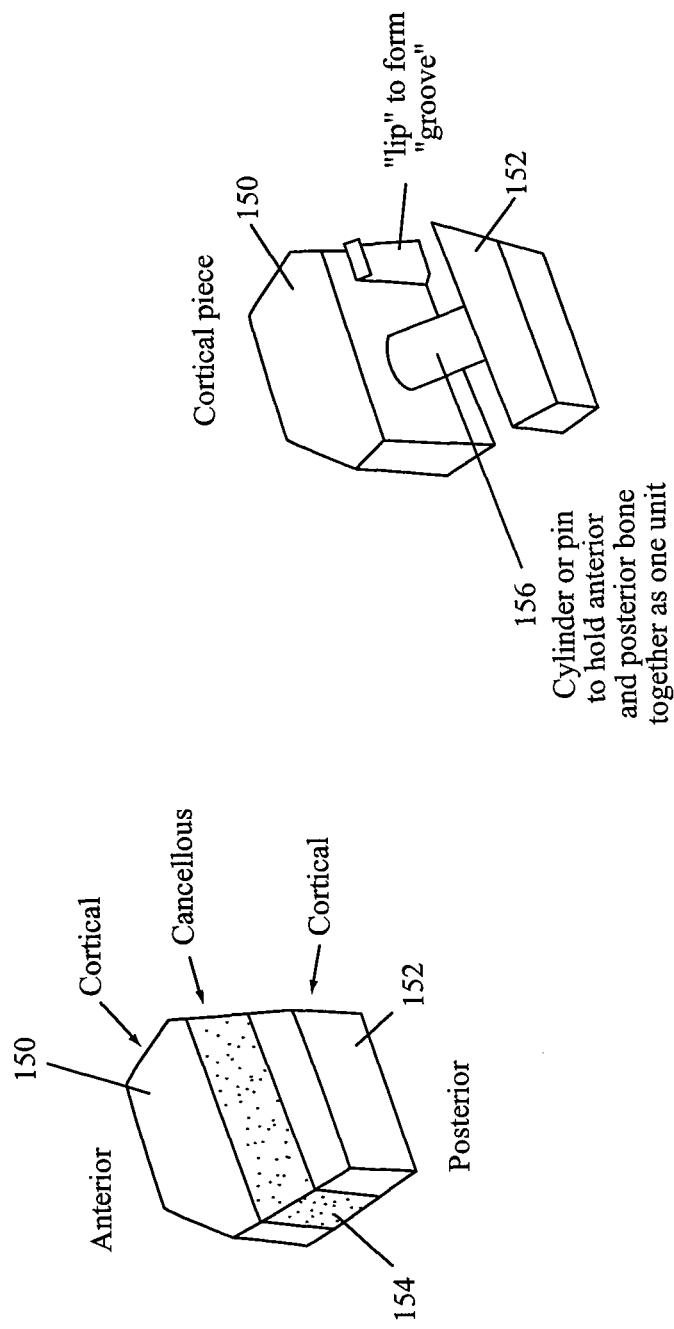
FIG. 17 is several views of an implant having a generally arc shaped center portion in accordance with an embodiment of the present invention.
Figure 18:
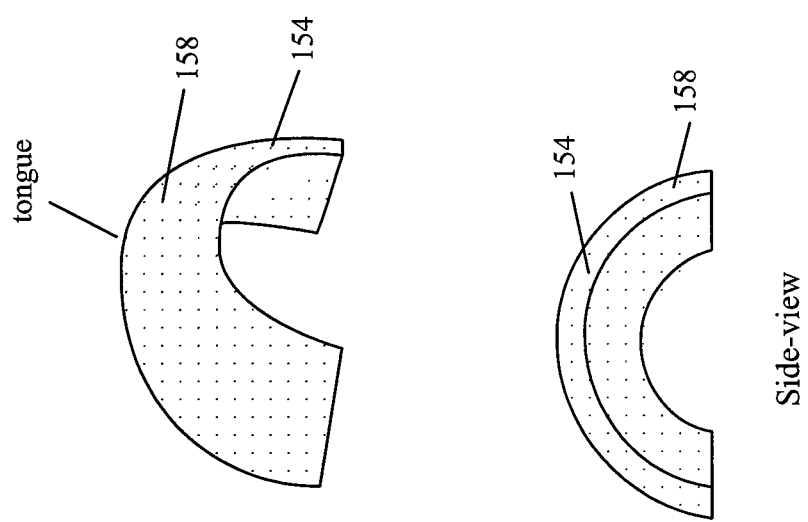
FIG. 18 is several views of a generally arc shaped center portion in accordance with an embodiment of the present invention of FIG. 17.

In yet another embodiment, illustrated in FIGS. 17 and 18, the implant may include spaced apart anterior and posterior portions 150, 152, respectively, that may be made of cortical bone. A center portion 154 may be made of cancellous bone. The center portion may be generally U-shaped, or arc shaped. The anterior and posterior cortical bone portions may be connected with a bone pin 156 or dowel, such that the bone pin may support the center cancellous portion. The bone pin may generally be centered within the inner surfaces of the anterior and posterior portions. In one embodiment, the spaced apart anterior and posterior cortical bone portions and the bone pin may be manufactured as a single piece. The cortical bone portion, including either or both of the anterior or posterior portion, may comprise a lip that forms a groove for a tongue and groove fit for the center cancellous portion. The cancellous portion may have a tongue 158, shown in FIG. 18, for mating with the groove of the cortical portion.

Generally, as can be seen from FIGS. 17 and 18, the center cancellous portion 154 may be shaped to fit into a cylindrical section of the cortical portion (including either of the anterior portion 150 or the posterior portion 152). The cancellous portion 154 may rotate into the final position, wherein the tongue 158 mates with the groove. When fully assembled, the inferior surface (or superior surface) of the implant may have a gap that results from the open portion of the arc-shaped cancellous portion. The gap may be plugged or filled with additional bone, if desired. In other embodiments, the gap may not be plugged.

Figure 19:
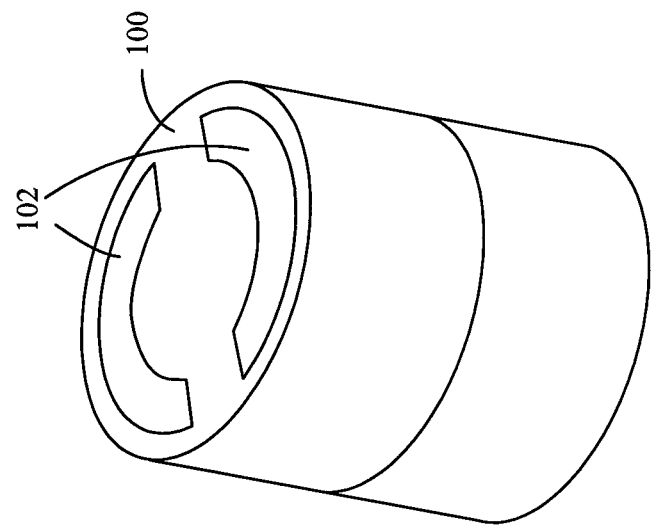
FIG. 19 is several views of an implant having center portions having arced outer surfaces in accordance with an embodiment of the present invention.
Figure 19:
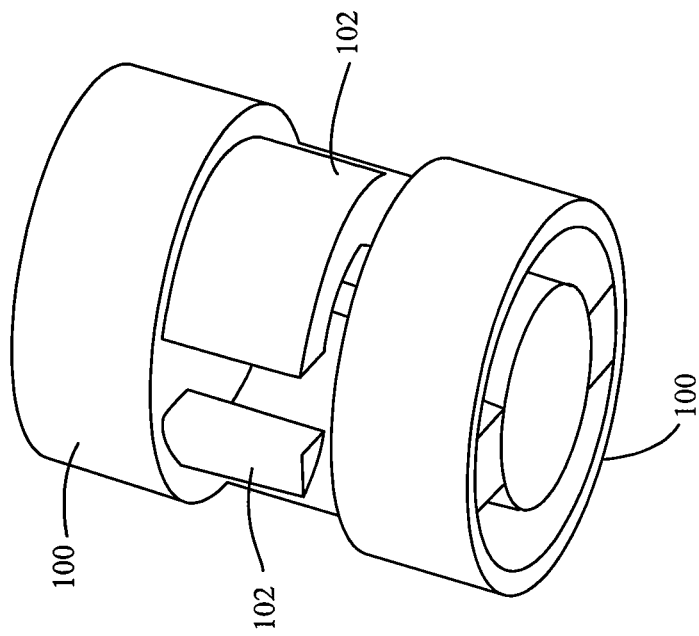
Figure 20:
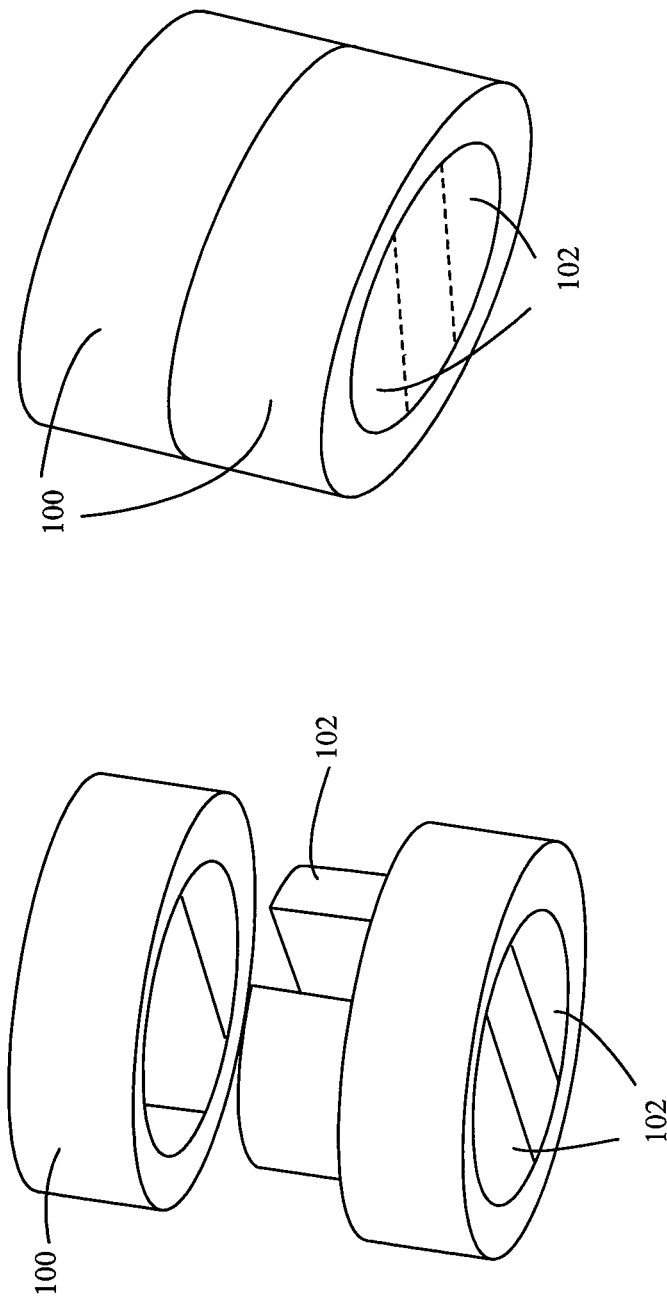
FIG. 20 is several views of an implant having center portions with arced outer surfaces in accordance with another embodiment of the present invention.

In an embodiment, such as that illustrated in FIGS. 19 and 20, an implant of the present disclosure may include a cortical body portion combined with one or more arced cancellous bone portions 102. The cancellous bone portions may be concentrically arced on two opposing sides (FIG. 19), or may be arced on one side and have a different surface, such as a flat surface, on the opposing side (FIG. 20). The cortical body portion may be generally cylindrical. However, it is recognized that the cortical body portion may be any suitable shape. The cortical bone portion may further comprise one or more similarly shaped cortical bone pieces 100 that may be joined together using the one or more arced cancellous bone portions 102. The cortical bone portion may have one or more arced slots for receiving the one or more arced cancellous bone portions. In an embodiment having more than one cortical bone pieces, each cortical bone piece may comprise one or more arced slots that align with the arced slots in the other cortical bone pieces. In one embodiment, there may be two cortical bone pieces that may be joined to form the cortical bone portion. In a further embodiment, there may be two arced cancellous bone portions. The cancellous bone portions may be received in the arced slots by, for example, press fit.

Figure 21:
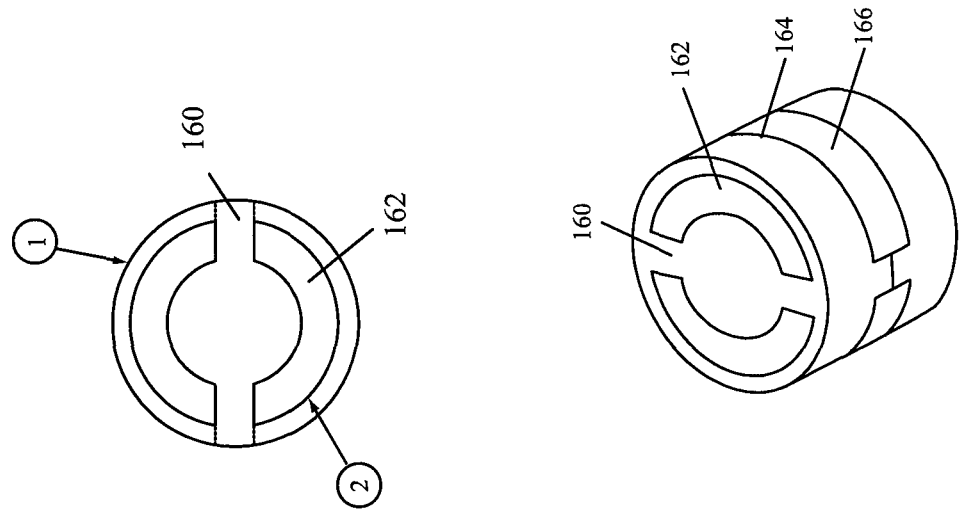
FIGS. 21, 22, and 23 are several views of an implant having center portions with arced outer surfaces in accordance with yet another embodiment of the present invention.
Figure 21:
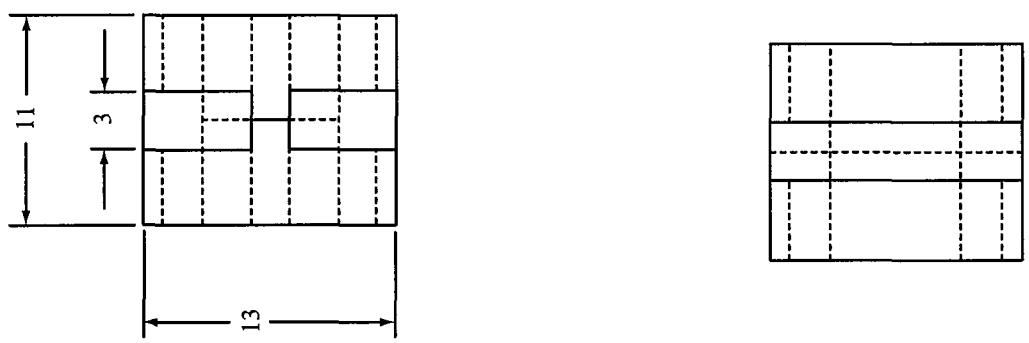
Figure 22:
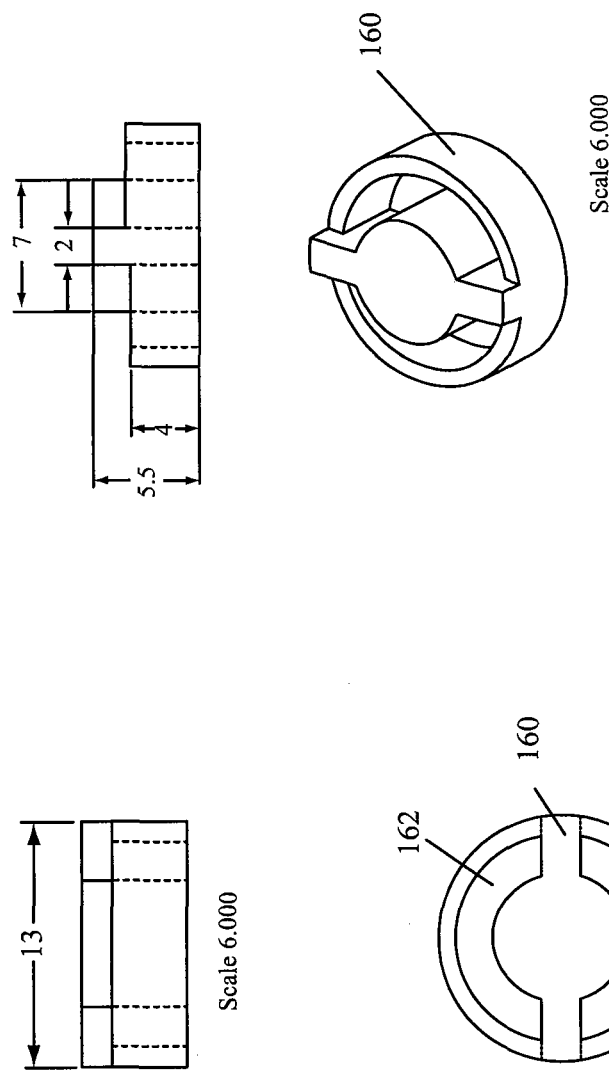
Figure 23:
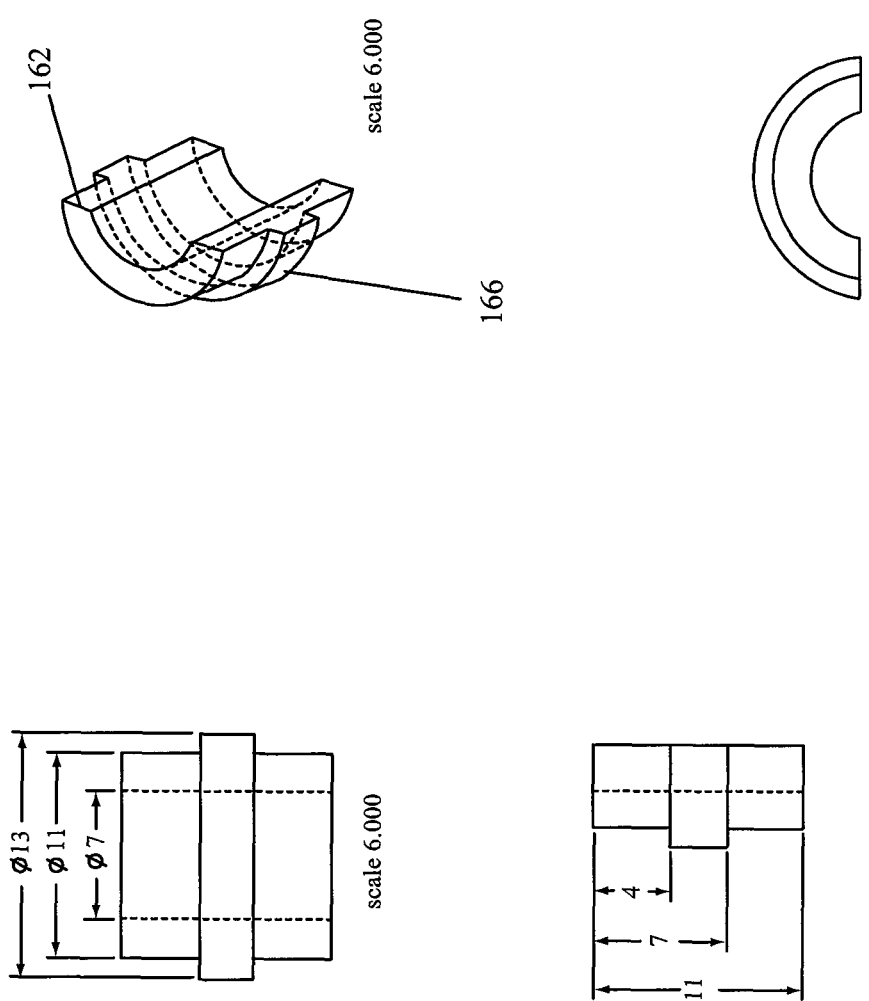

In a variation of the previous embodiment, illustrated in FIGS. 21, 22, and 23, an implant of the present disclosure may include a cortical body portion combined with one or more arced cancellous bone portions. In discussions of FIGS. 21, 22, and 23, the cortical portions are labeled as 160 and the cancellous portions are labeled as 162. The configurations of the cortical portions 160 and cancellous portions 162 may vary. The cancellous bone portions may be concentrically arced on two opposing sides, or may be arced on one side and have a different surface, such as a flat surface, on the opposing side The cortical bone portion may comprise two or more similarly shaped cortical bone pieces that may be joined together using the one or more arced cancellous bone portions. The cortical body portion may be generally cylindrical. However, it is recognized that the cortical body portion may be any suitable shape. The cortical bone portions may have one or more arced slots for receiving the one or more arced cancellous bone portions. In one embodiment, there may be two cortical bone pieces that may be joined to form the cortical bone portion. In a further embodiment, there may be two arced cancellous bone portions. As can be seen from FIGS. 21, 22, and 23, the cortical bone portions may comprise slots or openings 164 for receiving protrusions 166 that may be formed on outer arced surfaces of the cancellous bone portions 162. The openings on the cortical bone portions and the protrusions on the cancellous bone portions may further maintain the cortical and cancellous bone portions in a combined configuration. The cancellous bone portions may be received in the arced openings 164 by, for example, press fit.

Figure 24:
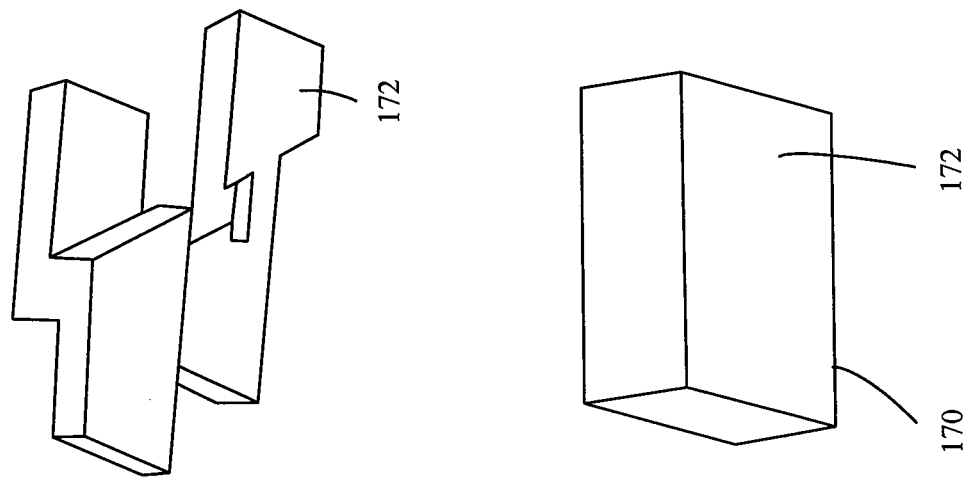
FIG. 24 is several views of an implant having a puzzle-like interface in accordance with an embodiment of the present invention.
Figure 24:
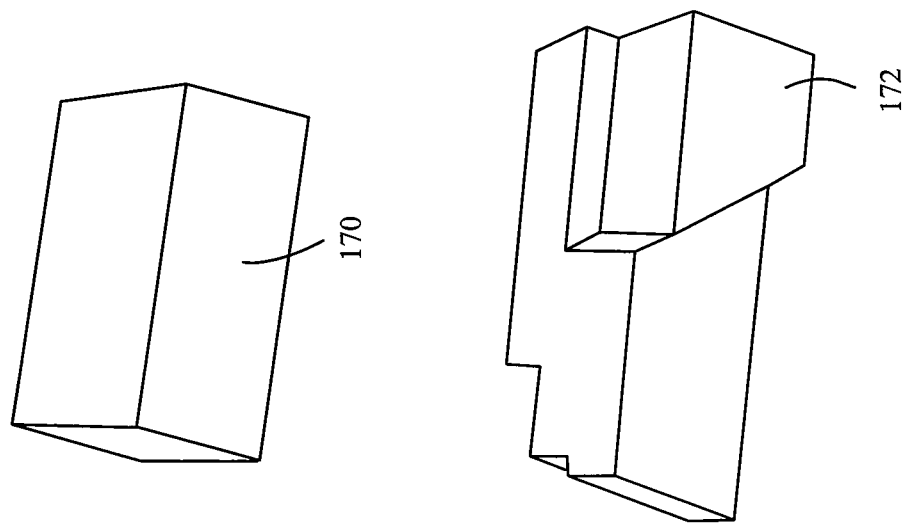

In another embodiment, illustrated in FIG. 24, a puzzle-like design may be used. In one embodiment, one portion 170 of the implant may be cortical bone or other structural biomaterial including any structural polymer, and a second portion 172 may be cancellous bone. In some embodiments, more than two portions may be used. Furthermore, any combination of cortical and cancellous bone may be used. As shown in FIG. 24, the cortical bone portion and the cancellous bone portion may slide together. Thus, the cortical bone portion and the cancellous bone portion may remain together without separating in the vertical direction. The two portions may be configured such that portions of both the cortical bone portion and the cancellous bone portion are at each of the inferior and superior surfaces.

Figure 25:
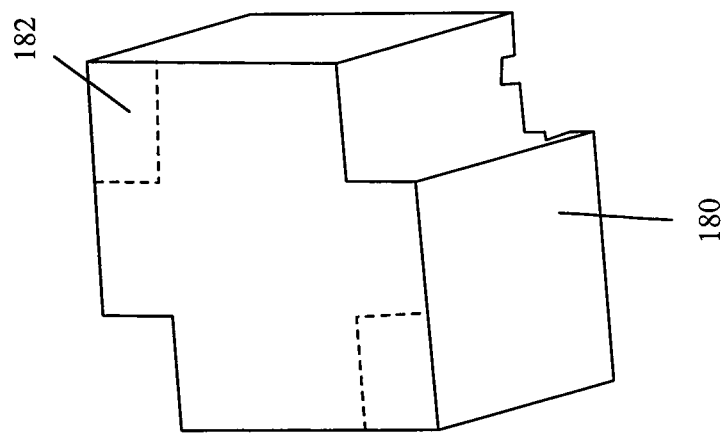
FIG. 25 is several views of an implant having a puzzle-like interface in accordance with another embodiment of the present invention.
Figure 25:
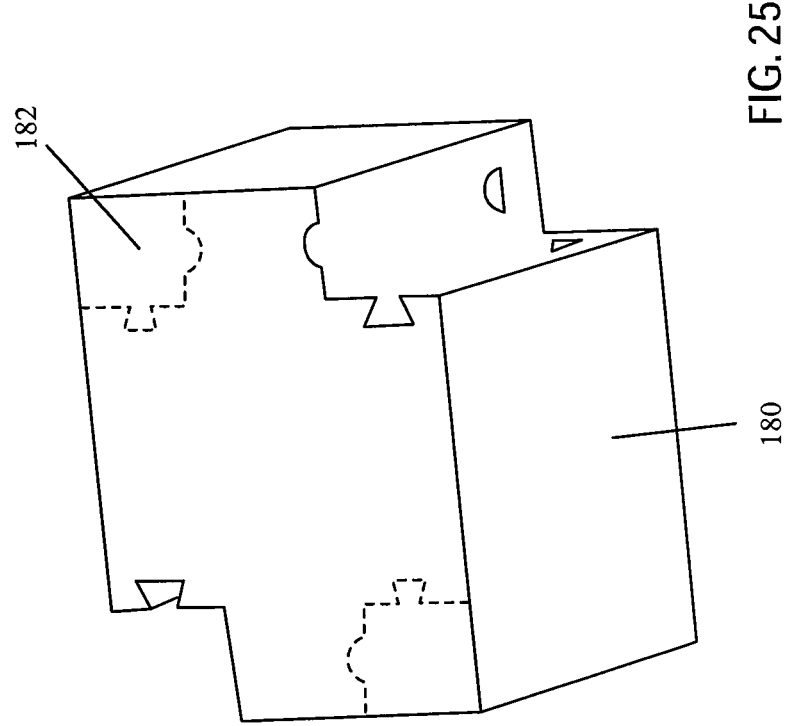

In an embodiment, illustrated in FIG. 25, a different puzzle-like design may be used. A center portion 180 of the implant may be cortical bone or other structural biomaterial including any structural polymer, and one or more corner portions 182 may be cancellous bone. In some embodiments, more than two portions may be used. Furthermore, any combination of cortical and cancellous bone may be used. As shown in FIG. 25, the center cortical bone portion and the corner cancellous bone portions may slide together. Thus, the cortical bone portion and the cancellous bone portion may remain together without separating in the medial/lateral and anterior/posterior directions. The two portions may be configured such that portions of both the cortical bone portion and the cancellous bone portion are at each of the inferior and superior surfaces. The cortical bone portion and the corner cancellous bone portions may combine to form any shape, such as but not limited to, circular, square, rectangular, trapezoidal, polygonal, etc. In one embodiment, as illustrated in FIG. 25, the cortical bone portion may be generally cross-shaped or "X" shaped, and four corner cancellous bone portions may combine with the cortical bone portion to generally form a square or rectangle.

In an embodiment, the center cortical bone portion may comprise slots or grooves for mating with protrusions of the corner cancellous bone portions. The slots, in one embodiment, may not extend the entire distance between the superior and inferior surfaces. In other embodiments, the slots may span from the superior surface to the inferior surface. A slot may be a dovetail, square, rectangular, circular or semi-circular, any other suitable shape, or any combination thereof, as illustrated in FIG. 25. The cortical bone portion may comprise any suitable number of slots. In one embodiment, the cortical bone portion comprises a slot on each surface that mates with a surface of a corner cancellous bone portion. The corner cancellous bone portions may comprise one or more protrusions. The protrusions may mate with the slots of the cortical bone portion. In one embodiment, each corner cancellous bone portion may comprise a slot on each surface that mates with a surface of the cortical bone portion.

Figure 26:
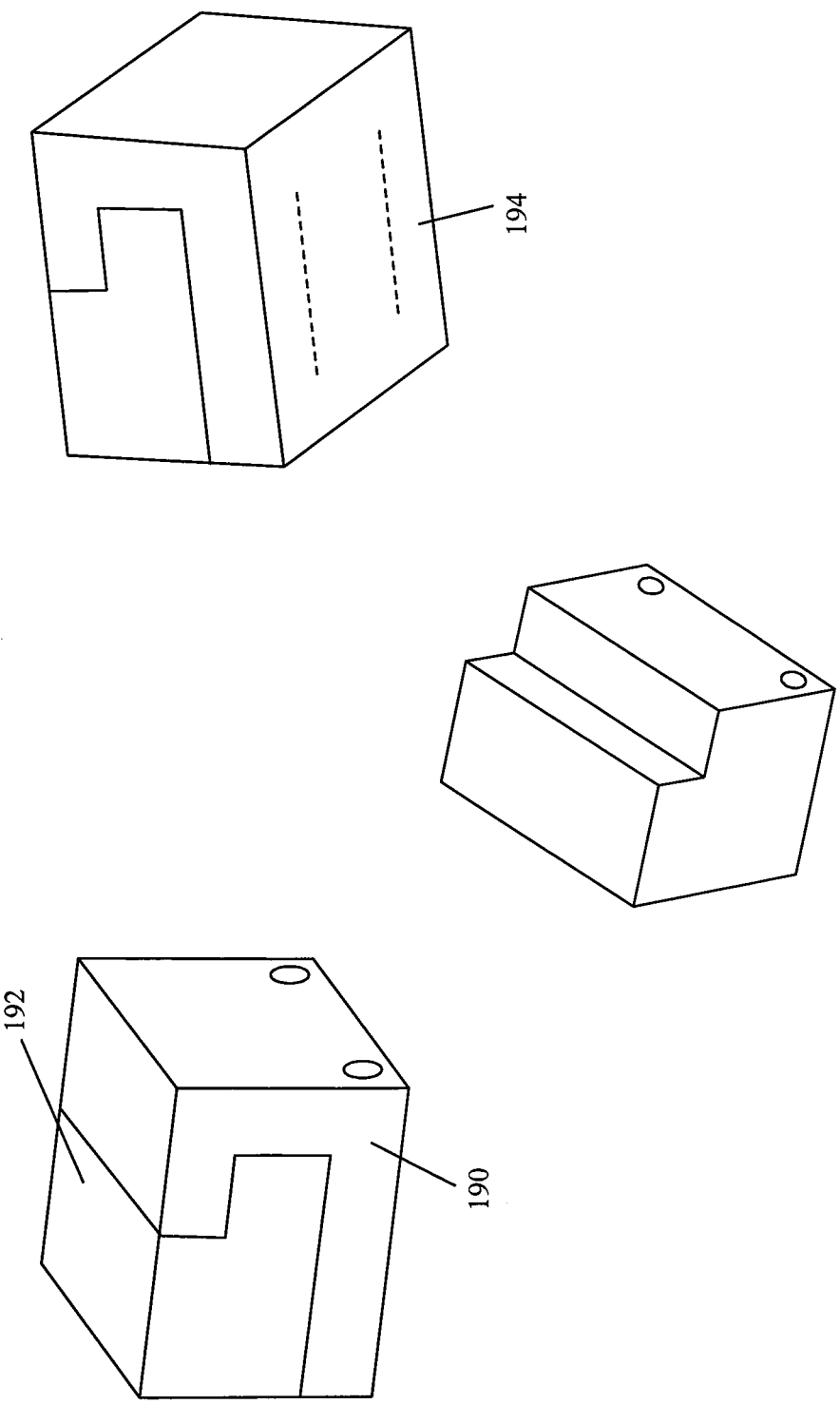
FIG. 26 is several views of an implant having a puzzle-like interface in accordance with a further embodiment of the present invention.

In another puzzle-like embodiment, illustrated in FIG. 26, one or more portions 190 of the implant may be cortical bone or other structural biomaterial including any structural polymer, and a portion 192 of the implant may be cancellous bone. However, any combination of cortical and cancellous bone may be used. In some embodiments, two portions of cortical bone may be used. A first cortical bone portion may generally be U-shaped. Each leg may generally have a square or rectangular cross section. However, it is recognized that the first cortical bone portion may be other shapes, including arc-shaped, the cross-section may similarly be other shapes. A second cortical bone portion may comprise a ledge section, such that when combined with the first cortical bone portion, a slot may be formed between the first cortical bone portion and the ledge section of the second cortical bone portion. The cortical bones portions may be secured together using dowels or pins. the dowels may be cortical bone or other structural biomaterial including any structural polymer. The cancellous portion of the implant may fit, or be press-fit with the cortical bone portions, such that the a ledged or protruding portion of the cancellous bone portion fits in the slot created between the first cortical bone portion and the ledge section of the second cortical bone portion. In a further embodiment, a portion of the cancellous bone portion may fit within the innerwalls of the U-shaped first cortical bone portion, as illustrated in FIG. 26. Thus, the cortical bone portion and the cancellous bone portion may remain together without separating in either the vertical or horizontal directions. The portions may be configured such that portions of both the cortical bone portions and the cancellous bone portion are at each of the inferior and superior surfaces. The osteoimplant may have a section 194 that is an insert or that is a surface of one of the other portions.

Figure 27:
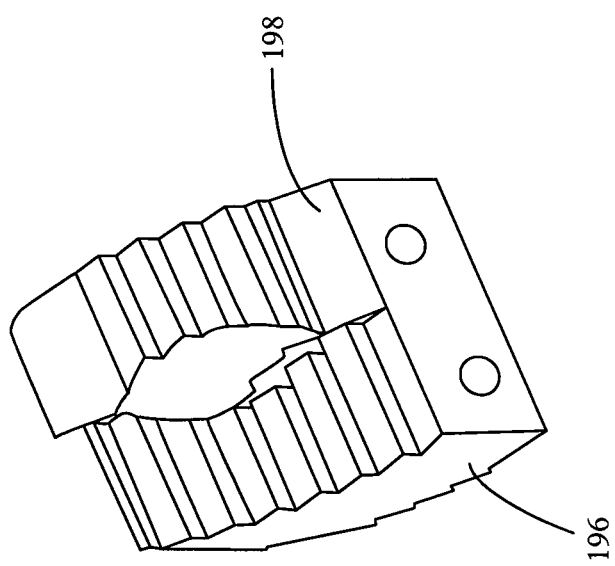
FIG. 27 is a perspective view of an implant having a dovetail interface in accordance with another embodiment of the present invention.

In yet another embodiment, an implant may comprise two or more bone portions 196, 198 having a dovetailed interface, such that the two or more bone portions may be slidably connected. That is, each of the bone portions may interface together so that a dovetail cut-out on one bone portion receives a dovetail on another bone portion. As illustrated in FIG. 27, the two or more bone portions may comprise cortical bone. However, it is recognized that any other suitable material such as cancellous bone or other biomaterial or polymer may be used for one or more of the bone portions. In further embodiments, the portions may have another suitable interface other than a dovetailed interface, such as a tongue and groove or other suitable joint. An implant comprising a slidable interface, such as a dovetail or tongue and groove joint, may allow for less invasive implant procedures. For example, each bone portion may be inserted into the implant site separately and may be slidably joined together at or in the implant site. The implant may be used, for example, as a posterior ramp implant.

Figure 28:
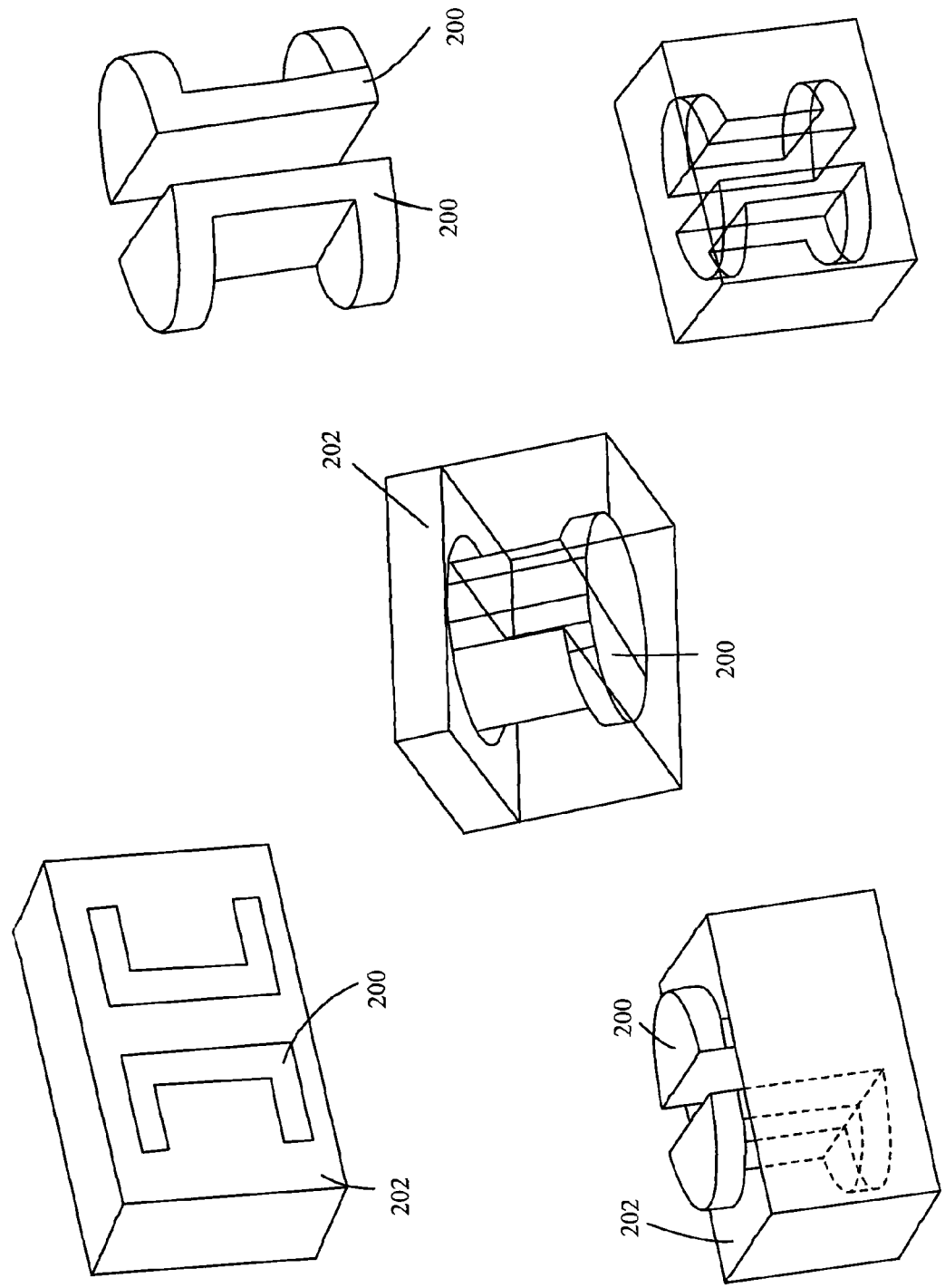
FIG. 28 is several views of an implant having a random shape center portion in accordance with an embodiment of the present invention.

In another embodiment, illustrated in FIG. 28, an embodiment of the implant of the present disclosure may comprise an implant having a center 200 portion of any variation, or shape, and an outer portion 202 adapted to receive the center bone portion. Either bone portion may comprise cortical or cancellous bone, or any other biomaterial or polymer. In further embodiments, such as that shown in FIG. 28, the implant may comprise more than one center portion 200. Similarly, the outer bone portion may comprise more than one piece. In one embodiment, the center portions comprise cancellous bone while the outer portion or portions comprise cortical bone. As one example of shapes that may be used, an implant illustrated in FIG. 28, may have two center cancellous bone portions. Each cancellous bone portion may comprise top and bottom portions having a generally half-circle shape and a connecting portion, orthogonal to the top and bottom portions, having a generally rectangular shape. Each cancellous portion may be fit, or press-fit, into an opening formed by one or more outer cortical bone portions adapted to receive the cancellous portions. In some embodiments, after the cancellous bone portions have been combined with the cortical bone portions, the implant may be shaped to the desired size and configuration.

Figure 29:
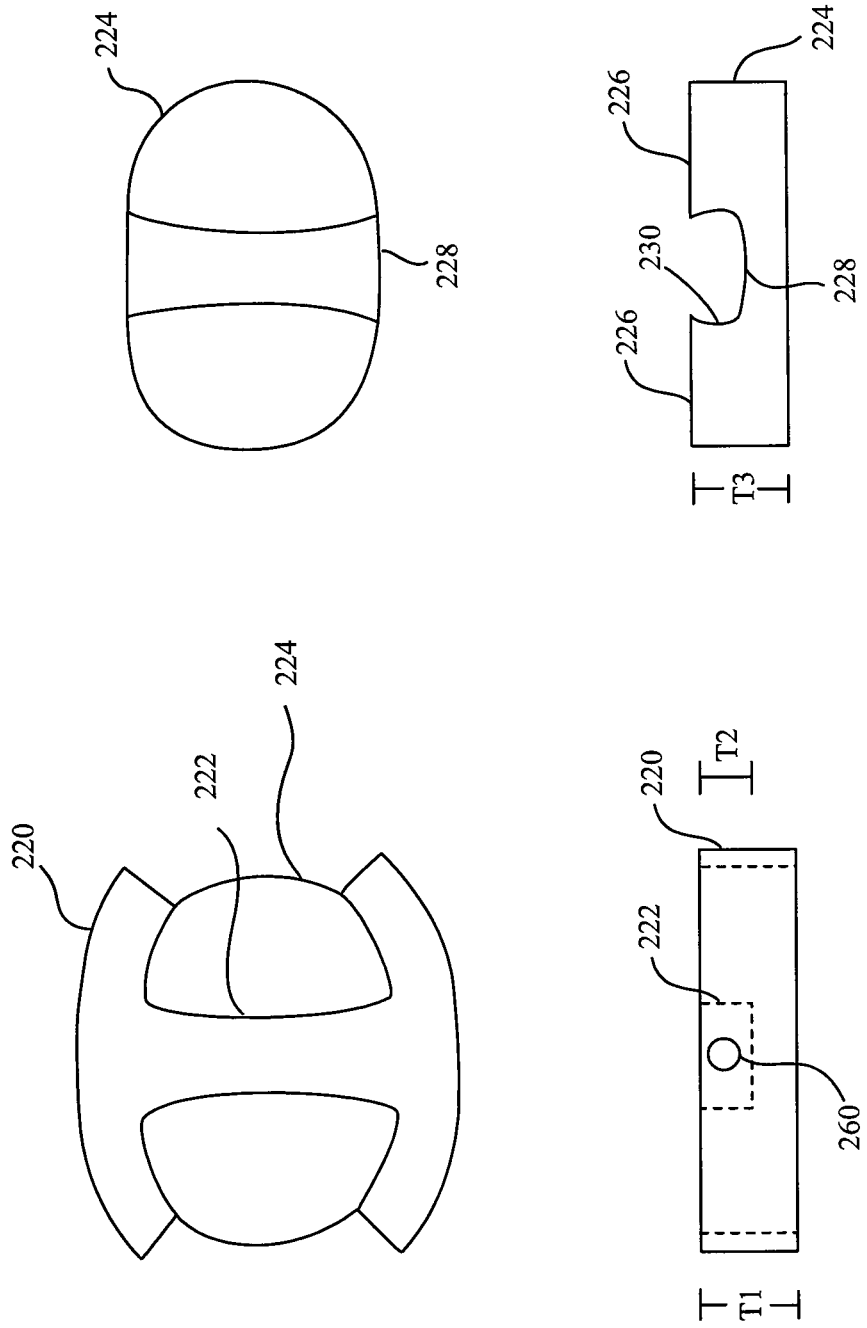
FIG. 29 illustrates an implant including press fit portions in accordance with a further embodiment of the present invention.

In another embodiment, illustrated in FIG. 29, an embodiment of the implant of the present disclosure may comprise an implant having a generally I-beam-shaped portion 220, as viewed from the top or bottom. In other embodiments, an implant may comprise a portion comprising a different suitable shape, such as but not limited to, a generally Z-shaped or N-shaped portion, an I-beam-shaped portion having broadened sides or ends, a generally T-shaped or Y-shaped portion, or any other shaped portion suitable for interlocking with at least a second portion of the implant. In one embodiment, the second portion may comprise recessed areas, described in further detail below, for receiving one or more stem portions, including straight, curved, jagged, zig-zagged, etc. stem portions, of the I-beam-shaped (or other shaped) portion in an interlocking manner, such as by but not limited to press-fit or snap-fit. For the reason of exemplarily describing one embodiment of an osteoimplant in accordance with the present disclosure, only an implant having an I-beam-shaped portion 220 is described and illustrated. However, it is recognized that the features of an I-beam-shaped portion 220 described herein may be similarly embodied in differently shaped portions. The I-beam-shaped portion 220 may have straight edges or may have curved edges on the top and bottom edges of the "I" as viewed from the top or bottom. Similarly, the I-beam-shaped portion 220 may have straight edges or may have curved edges on the center stem 222 of the "I" as viewed from the top or bottom. As illustrated in FIG. 29, as viewed from the side, the I-beam-shaped portion 220 may have a total thickness T1. In one embodiment, a portion of the center stem 222 may have a thickness T2 that is less than the total thickness T1 of the I-beam-shaped portion 220. The implant illustrated in FIG. 29 may further have a connecting portion 224 that may fit together with the I-beam-shaped portion 220. In a further embodiment, the connecting portion 224 may, for example, fit, press-fit, or snap-fit with the I-beam-shaped portion 220. The connecting portion 224 may be generally circular, ovoid, rectangular, or any other suitable shape. As illustrated in FIG. 29, the connecting portion 224 may be substantially oval. The connecting portion 224 may have raised outer edges 226 and a recessed center section 228. The outer edges 226 and the center section 228 may combine to allow the connecting portion 224 to press-fit or snap-fit into/onto the I-beam-shaped portion 220. For example, in one embodiment, the center stem 222 of the I-beam-shaped portion 220 may snap into/onto the recessed center section 228 and between outer edges 226 of the connecting portion 224. In one embodiment, the thickness T3 of the outer edges 226 may be substantially the same as total thickness T1 of the I-beam-shaped portion 220. Similarly, the combined thickness of each portion along the center stem 222 and each corresponding portion along the recessed center section 228 may be substantially the same as the total thickness T1 of the I-beam-shaped portion 220. In a further embodiment, as illustrated in FIG. 29, the inner side walls 230 of the outer edges 226 in the area of the recessed section 228 may be straight or curved. In one embodiment, the inner side walls 230 may be concave side walls. Curved inner side walls may help maintain the I-beam-shaped portion 220 and the connecting portion 224 in a press fit or snapped together manner. Either portion may comprise cortical or cancellous bone, or any other biomaterial or polymer. In one embodiment, the I-beam-shaped portion 220 may be cortical bone, and the connecting portion 224 may be cancellous bone.

Figure 30:
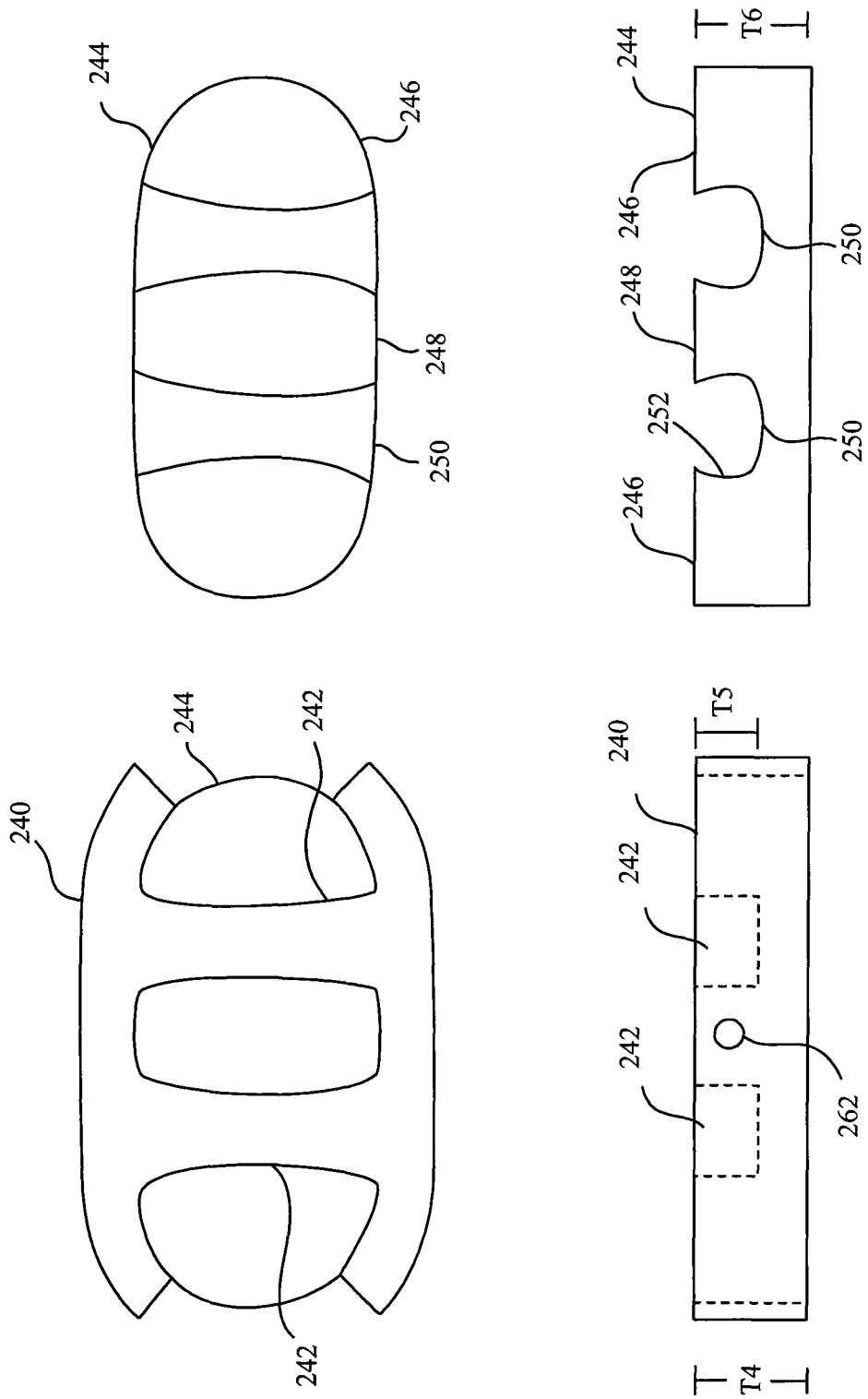
FIG. 30 illustrates an implant including press fit portions in accordance with yet another embodiment of the present invention.

In another embodiment illustrated in FIG. 30, an embodiment of the implant of the present disclosure may comprise an implant having a generally double I-beam-shaped portion 240, as viewed from the top or bottom. In other embodiments, an implant may comprise a portion comprising a different suitable shape, such as but not limited to, a generally Z-shaped or N-shaped portion, an I-beam-shaped portion having broadened sides or ends, a generally T-shaped or Y-shaped portion, or any other shaped portion suitable for interlocking with at least a second portion of the implant. In one embodiment, the second portion may comprise recessed areas, described in further detail below, for receiving one or more stem portions, including straight, curved, jagged, zig-zagged, etc. stem portions, of the double I-beam-shaped (or other shaped) portion in an interlocking manner, such as by but not limited to press-fit or snap-fit. For the reason of exemplarily describing one embodiment of an osteoimplant in accordance with the present disclosure, only an implant having a double I-beam-shaped portion 240 is described and illustrated. However, it is recognized that the features of a double I-beam-shaped portion 240 described herein may be similarly embodied in differently shaped portions. The double I-beam-shaped portion 240 may have straight edges or may have curved edges on the top and bottom edges of the "I"s as viewed from the top or bottom. Similarly, the double I-beam-shaped portion 240 may have straight edges or may have curved edges on the center stems 242 of the "I"s as viewed from the top of bottom. In yet further embodiments, an implant of the present disclosure may have more than two center stems. For example a triple I-beam-shaped portion, quadruple I-beam-shaped portion, or any other suitable multiple I-beam-shaped portion may be used in the implant of the present disclosure. As illustrated in FIG. 30, as viewed from the side, the double I-beam-shaped portion 240 may have a total thickness T4. In one embodiment, a portion of the center stems 242 may have a thickness T5 that is less than the total thickness T4 of the double I-beam-shaped portion 240. Furthermore, each center stem 242 may have a different thickness than the other center stems 242. The implant illustrated in FIG. 30 may further have a connecting portion 244 that may fit together with the double I-beam-shaped portion 240. In a further embodiment, the connecting portion 244 may, for example, fit, press-fit, or snap-fit with the double I-beam-shaped portion 240. The connecting portion 244 may be generally circular, ovoid, rectangular, or any other suitable shape. As illustrated in FIG. 29, the connecting portion 244 may be substantially oval. The connecting portion 244 may have raised outer edges 246 and a raised center section 248. In embodiments where more than two center stems are included in the I-beam-shaped portion 240, more raised sections 248 may be included on the connection portion 244. The connecting portion 244 may have recessed center sections 250. In embodiments where more than two center stems are included in the I-beam-shaped portion 240, more recessed sections 250 may be included on the connection portion 244. The outer edges 246, raised sections 248, and the recessed sections 250 may combine to allow the connecting portion 244 to press-fit or snap-fit into the double I-beam-shaped portion 240. For example, in one embodiment, the center stems 242 of the double I-beam-shaped portion 240 may snap into the recessed center sections 250 and between outer edges 246 and raised center section 248 of the connecting portion 244. In one embodiment, the thickness T6 of the outer edges 246 and raised center section 248 may be substantially the same as total thickness T4 of the double I-beam-shaped portion 240. Similarly, the combined thickness of each portion along the center stems 242 and each corresponding portion along the recessed sections 250 may be substantially the same as the total thickness T4 of the double I-beam-shaped portion 240. In a further embodiment, as illustrated in FIG. 30, the inner side walls 252 of the outer edges 246 and raised center section 248 in the area of the recessed sections 250 may be straight or curved. In one embodiment, the inner side walls 252 may be concave side walls. Curved inner side walls may help maintain the double I-beam-shaped portion 240 and the connecting portion 244 in a press fit or snapped together manner. Either portion may comprise cortical or cancellous bone, or any other biomaterial or polymer. In one embodiment, the double I-beam-shaped portion 240 may be cortical bone, and the connecting portion 244 may be cancellous bone.

The embodiments of an osteoimplant described and illustrated herein may further include a inserter connection location for an implant insertion device, wherein the insertion device, or inserter, may be used to position the implant within the desired surgical area. The inserter connection location may be located at any suitable location of the implant. In some embodiments, the connection location may be located in a location of the implant wherein the insertion load may be transmitted across one or more components of the implant device. In further embodiments, the inserter connection location may be located generally in a location of the implant wherein the insertion load may be transmitted across a load bearing or load resisting component of the implant. In one embodiment, the inserter connection location may comprise a hole for receiving an end of the insertion device. In some embodiments, the insertion device may fit, such as press-fit or snap-fit, into the inserter connection location. In other embodiments, the inserter connection location may comprise a threaded hole for receiving a threaded end of an insertion device. In further embodiments yet, the inserter connection location may comprise any suitable means for connecting an insertion device to the implant, such as adhesive, etc.

For example, as illustrated in the embodiments of FIGS. 29 and 30, I-beam-shaped portions 220 and 240 may comprise inserter connection locations 260 and 262, respectively. The inserter connection locations may be located on a top (or bottom) edge, such that the insertion load can be transmitted generally along a long axis of the I-beam-shaped portions 220 and 240. The inserter connection locations may comprise a hole, a threaded hole, or any other suitable means for connection the inserter device to the implant, such as adhesive, etc. Similar inserter connection locations may be utilized with other embodiments of the osteoimplant described herein.

Although the present invention has been described with reference to preferred embodiments, persons skilled in the art will recognize that changes may be made in form and detail without departing from the spirit and scope of the invention. For example, in the various embodiments described herein, the cortical bone portions and the cancellous bone portions may be switched, such that the bone portions described above in relation to cortical bone may be replaced with cancellous bone and the bone portions described above in relation to cancellous bone may be replaced with cortical bone.

We claim:

1. An osteoimplant comprising a plurality of first portions and a second portion, wherein the portions are threadingly engaged with one another to form the desired osteoimplant,
wherein the second portion extends along an axis between a first end surface and a second end surface, at least one of the end surfaces including a plurality of ridges configured to engage bone, the second portion including an inner surface defining a plurality of recessed sections extending parallel to the axis for receiving the plurality of first portions,
wherein at least one of the plurality of recessed sections only partially extend into the second portion such that the plurality of first portions are spaced apart from at least one of the first and second end surfaces when the plurality of first portions are disposed in the plurality of recessed sections, and
wherein the second portion comprises particles of cortical bone and the first portion comprises particles of cancellous bone, the osteoimplant comprising approximately 10% to about 95% particles of cortical and cancellous bone by weight,
wherein each of the plurality of recessed sections extends along a second axis, and
wherein at least two of the second axes of the plurality of the recessed sections are transverse to each other.

2. The osteoimplant of claim 1, wherein the recessed section and the first portion are configured such that the first portion partially extends from the first end surface or the second end surface of the second portion.

3. The osteoimplant of claim 1, wherein the osteoimplant comprises approximately 50% to approximately 80% particles of cortical and cancellous bone by weight.

4. The osteoimplant of claim 1, wherein the osteoimplant comprises approximately 50% particles of cortical and cancellous bone by weight.

5. The osteoimplant of claim 1, wherein the osteoimplant comprises approximately 65% particles of cortical and cancellous bone by weight.

6. The osteoimplant of claim 1, wherein at least one of the particles of cortical bone and the particles of cancellous bone comprises lightly demineralized bone particles.

7. The osteoimplant of claim 1, wherein at least one of the particles of cortical bone and the particles of cancellous bone comprises deorganified bone particles.

8. The osteoimplant of claim 1, wherein the osteoimplant comprises a plasticizer configured to make the osteoimplant more pliable.

9. The osteoimplant of claim 8, wherein the plasticizer comprises PEG 6000, or PEG 8000.

10. The osteoimplant of claim 1, wherein the osteoimplant comprises a porogen configured to diffuse, dissolve or degrade after implantation of the osteoimplant leaving a pore.

11. The osteoimplant of claim 10, wherein the porogen comprises a gas comprising carbon dioxide or nitrogen.

12. The osteoimplant of claim 10, wherein the porogen comprises a carbohydrate.

13. The osteoimplant of claim 10, wherein the porogen comprises a polymer.

14. The osteoimplant of claim 1, wherein the recessed section is a blind hole that extends through the first end surface without extending through the second end surface.

15. The osteoimplant of claim 1, wherein the osteoimplant comprises a polymer component.

16. The osteoimplant of claim 15, wherein the polymer component includes PEG blended, grafted, or co-polymerized with the polymer.

17. The osteoimplant of claim 1, wherein at least one of the particles of cortical bone is configured to resist mechanical loads.

18. The osteoimplant of claim 1, wherein at least one of the particles of cancellous bone is substantially non-porous.

19. The osteoimplant of claim 1, wherein the threadingly engaged portions define threads that are continuous.

20. The osteoimplant of claim 1, wherein the threadingly engaged portions define threads that are discontinuous.

* * * * *